(12) United States Patent
Boudewijns et al.

(10) Patent No.: US 11,680,084 B2
(45) Date of Patent: Jun. 20, 2023

(54) LIVE-ATTENUATED FLAVIRUSES WITH HETEROLOGOUS ANTIGENS

(71) Applicant: KATHOLIEKE UNIVERSITEIT LEUVEN, Leuven (BE)

(72) Inventors: Robbert Boudewijns, Essen (BE); Kai Dallmeier, Kessel-Lo (BE); Johan Neyts, Kessel-Lo (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 73 days.

(21) Appl. No.: 16/753,364

(22) PCT Filed: Oct. 5, 2018

(86) PCT No.: PCT/EP2018/077157
§ 371 (c)(1),
(2) Date: Apr. 3, 2020

(87) PCT Pub. No.: WO2019/068877
PCT Pub. Date: Apr. 11, 2019

(65) Prior Publication Data
US 2020/0331969 A1 Oct. 22, 2020

(30) Foreign Application Priority Data

Oct. 5, 2017 (GB) .................................... 1716254

(51) Int. Cl.
*C07K 14/005* (2006.01)
*A61K 39/00* (2006.01)

(52) U.S. Cl.
CPC ........ *C07K 14/005* (2013.01); *A61K 2039/53* (2013.01); *A61K 2039/572* (2013.01); *C07K 2319/00* (2013.01); *C12N 2770/24121* (2013.01); *C12N 2770/24134* (2013.01)

(58) Field of Classification Search
None
See application file for complete search history.

(56) References Cited

U.S. PATENT DOCUMENTS

2008/0318208 A1* 12/2008 Puffer ...................... C12Q 1/70
435/5
2013/0156818 A1* 6/2013 de los Rios .......... A61K 31/713
424/400

FOREIGN PATENT DOCUMENTS

WO      2005042014 A1      5/2005
WO      WO08076290    *    6/2008
WO      2014174078 A1     10/2014

OTHER PUBLICATIONS

International Search Report in reference to co-pending European Patent Application No. PCT/EP2018/077157 filed Oct. 5, 2018.
International Search Report and Written Opinion in reference to co-pending European Patent Application No. PCT/EP2018/077157 filed Oct. 5, 2018.
Stoyanov C T et al: Immunogenicity and protective efficacy of a recombinant yellow fever vaccine against the murine malarial parasite Plasmodium yoelii11 , Vaccine, Els ev i er, Amsterdam, vol. 28, No. 29, pp. 4644-4652, Jun. 23, 2010, XP027474780.
Rasala Beth A et al: "Robust Expression and Secretion of Xylanasel in Chlamydomonas reinhardtii by Fusion to a Selection Gene and Processing with the FMDV 2A Peptide", PLOS ONE, vol. 7, No. 8, Aug. 1, 2012, XP002688993.
Weniger, et al., "Alternative vaccine delivery methods", Section Three: Vaccines in development and new vaccine strategies, pp. 1200-1231, 6th addition, 2013.
Bonaldo, et al., "The yellow fever 17D vims as a platform for new live attenuated vaccines", Human Vaccines & Immunotherapeutics, pp. 1256-1265, May 2014.
Chng, et al., "Cleavage efficient 2A peptides for high level monoclonal antibody expression in CHO cells", Bioprocessing Technology Institute, vol. 7, Issue 2, pp. 403-412, 2015.
Cicin-Sain, et al., "Vaccination of Mice with Bacteria Carrying a Cloned Herpesvirus Genome Reconstituted in Vivo", Journal of Virology, vol. 77, No. 15, pp. 8249-8255, Aug. 2003.
Darji, et al., "Oral delivery of DNA vaccines using attenuated *Salmonella* typhimurium as carrier", FEMS Immunology and Medical Microbiology, vol. 27, pp. 341-349, 2000.
Donnelly, et al., "The 'cleavage' activities of foot-and-mouth disease virus 2A site-directed mutants and naturally occurring '2A-like' sequences", Journal of General Virology, vol. 82, pp. 1027-1041, 2001.
Fischl, et al., "High-thoughput Screening Using Dengue Virus Reporter Genomes", Chapter 17, vol. 1030, pp. 205-219, 2013.
Jung, et al., "Activation of a Heterogenous Hepatitus B (HB) Core and e Antigen-Specific CD4+ T-Cell Population Turing Seroconversion to Anti-HBe and Anti-HBs in Hepatitus B Virus Infection", vol. 69, No. 6, pp. 3358-3368, Jun. 1995.
Samsa, et al., "Uncoupling cis-Acting RNA Elements from Coding Sequences revealed a Requirement of the N-Terminal Region of Dengue Virus Capsid Protein in Virus Particle Formation", Journals of Virology, vol. 86, No. 2, pp. 1046-1058, Jan. 2012.
Schoggins, et al., "Dengue reporter viruses reveal viral dynamics in interferon effectors in vitro", vol. 109, No. 36, pp. 14610-14615, Sep. 4, 2012.
Thimme, et al., "CD8+ T Cells Mediate Viral Clearance and Disease Pathogenesis during Acute Hepatitis B Virus Infection", Journal of Virology, vol. 77, No. 1, pp. 68-76, Jan. 2003.
Saltzman, et al., DNA Vaccines, Methods and Protocols, Methods in Molecular Medicin E, Second Edition, vol. 127, pp. 71-136, 2014.

* cited by examiner

*Primary Examiner* — Benjamin P Blumel
(74) *Attorney, Agent, or Firm* — Dinsmore & Shohl, LLP

(57) ABSTRACT

The invention relates to polynucleotides comprising the sequence of a flavivirus preceded by a sequence encoding an N terminal part of a flavivirus Capsid protein, an immunogenic protein, or a part thereof comprising a an immunogenic peptide, and a 2A cleaving peptide, and to the virus encoded by such sequences. The invention further relates to the use of such polynucleotides and viruses as vaccines.

22 Claims, 6 Drawing Sheets

Figure 1:
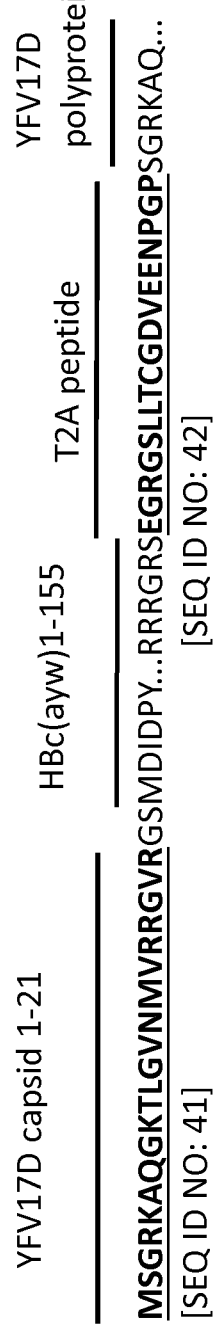

Specification includes a Sequence Listing.

SEQUENCE LISTING

<160> NUMBER OF SEQ ID NOS: 48

<210> SEQ ID NO 1
<211> LENGTH: 1744
<212> TYPE: DNA
<213> ORGANISM: Artificial Sequence
<220> FEATURE:
<223> OTHER INFORMATION: 5' end of YFV with heterologous antigen

<400> SEQUENCE: 1

```
agtaaatcct gtgtgctaat tgaggtgcat tggtctgcaa atcgagttgc taggcaataa    60
acacatttgg attaatttta atcgttcgtt gagcgattag cagagaactg accagaacat   120
gtctggtcgt aaagctcagg gaaaaacccct gggcgtcaat atggtacgac gaggagttcg   180
cggatccgtt taaacctcgt ccccgccggg tcacccggcc agcgacatgg aggcccagaa   240
taccctcctt gacagtcttg acgtgcgcag ctcaggggca tgatgtgact gtcgcccgta   300
catttagccc atacatcccc atgtataatc atttgcatcc atacattttg atggccgcac   360
ggcgcgaagc aaaaattacg gctcctcgct gcagacctgc gagcagggaa acgctcccct   420
cacagacgcg ttgaattgtc cccacgccgc gcccctgtag agaaatataa aaggttagga   480
tttgccactg aggttcttct ttcatatact tccttttaaa atcttgctag gatacagttc   540
tcacatcaca tccgaacata aacaaccatg acagtcaaca ctaagaccta tagtgagaga   600
gcagaaactc atgcctcacc agtagcacaa cgattatttc gattaatgga actgaagaaa   660
accaatttat gtgcatcaat tgatgttgat accactaagg aattccttga attaattgat   720
aaattgggtc cttatgtatg cttaatcaag actcatattg atataatcaa tgattttttcc   780
tatgaatcca ctattgaacc attattagaa ctttcacgta aacatcaatt tatgattttt   840
gaagatagaa aatttgctga tattggtaat accgtgaaga aacaatatat tggtggagtt   900
tataaaatta gtagttgggc agatattact aatgctcatg gtgtcactgg gaatggagta   960
gttgaaggat taaaacaggg agctaaagaa accaccacca accaagagcc aagagggtta  1020
ttgatgttag ctgaattatc atcagtggga tcattagcat atggagaata ttctcaaaaa  1080
actgttgaaa ttgctaaatc cgataaggaa tttgttattg gatttattgc ccaacgtgat  1140
atgggtggac aagaagaagg atttgattgg cttattatga cacctggagt tggattagat  1200
gataaaggtg atggattagg acaacaatat agaactgttg atgaagttgt tagcactgga  1260
actgatatta tcattgttgg tagaggattg tttggtaaag gaagagatcc agatattgaa  1320
ggtaaaaggt atagagatgc tggttggaat gcttatttga aaaagactgg ccaattataa  1380
tcagtactga caataaaaag attcttgttt tcaagaactt gtcatttgta tagttttttt  1440
atattgtagt tgttctattt taatcaaatg ttagcgtgat ttatattttt tttcgcctcg  1500
acatcatctg cccagatgcg aagttaagtg cgcagaaagt aatatcatgc gtcaatcgta  1560
tgtgaatgct ggtcgctata ctgtttaaac gagggacgcg ggtccctgct gacctgtggc  1620
gacgtggagg agaaccccgg tcctagcggc cgcaaagccc agggtaagac actgggcgtg  1680
aacatggttc gtcgcggcgt ccggtccttg tcaaacaaaa taaaacaaaa aacaaaacaa  1740
attg                                                                1744
```

<210> SEQ ID NO 2
<211> LENGTH: 21
<212> TYPE: PRT
<213> ORGANISM: artificial sequence
<220> FEATURE:
<223> OTHER INFORMATION: N terminal part of capsid

<400> SEQUENCE: 2

Met Ser Gly Arg Lys Ala Gln Gly Lys Thr Leu Gly Val Asn Met Val
1               5                   10                  15

Arg Arg Gly Val Arg
            20

<210> SEQ ID NO 3

<211> LENGTH: 270
<212> TYPE: PRT
<213> ORGANISM: artificial sequences
<220> FEATURE:
<223> OTHER INFORMATION: Hepatitis antigen

<400> SEQUENCE: 3

Met Thr Val Asn Thr Lys Thr Tyr Ser Glu Arg Ala Glu Thr His Ala
1               5                   10                  15

Ser Pro Val Ala Gln Arg Leu Phe Arg Leu Met Glu Leu Lys Lys Thr
            20                  25                  30

Asn Leu Cys Ala Ser Ile Asp Val Asp Thr Thr Lys Glu Phe Leu Glu
        35                  40                  45

Leu Ile Asp Lys Leu Gly Pro Tyr Val Cys Leu Ile Lys Thr His Ile
    50                  55                  60

Asp Ile Ile Asn Asp Phe Ser Tyr Glu Ser Thr Ile Glu Pro Leu Leu
65                  70                  75                  80

Glu Leu Ser Arg Lys His Gln Phe Met Ile Phe Glu Asp Arg Lys Phe
                85                  90                  95

Ala Asp Ile Gly Asn Thr Val Lys Lys Gln Tyr Ile Gly Gly Val Tyr
            100                 105                 110

Lys Ile Ser Ser Trp Ala Asp Ile Thr Asn Ala His Gly Val Thr Gly
        115                 120                 125

Asn Gly Val Val Glu Gly Leu Lys Gln Gly Ala Lys Glu Thr Thr Thr
    130                 135                 140

Asn Gln Glu Pro Arg Gly Leu Leu Met Leu Ala Glu Leu Ser Ser Val
145                 150                 155                 160

Gly Ser Leu Ala Tyr Gly Glu Tyr Ser Gln Lys Thr Val Glu Ile Ala
                165                 170                 175

Lys Ser Asp Lys Glu Phe Val Ile Gly Phe Ile Ala Gln Arg Asp Met
            180                 185                 190

Gly Gly Gln Glu Glu Gly Phe Asp Trp Leu Ile Met Thr Pro Gly Val
        195                 200                 205

Gly Leu Asp Asp Lys Gly Asp Gly Leu Gly Gln Gln Tyr Arg Thr Val
    210                 215                 220

Asp Glu Val Val Ser Thr Gly Thr Asp Ile Ile Ile Val Gly Arg Gly
225                 230                 235                 240

Leu Phe Gly Lys Gly Arg Asp Pro Asp Ile Glu Gly Lys Arg Tyr Arg
                245                 250                 255

Asp Ala Gly Trp Asn Ala Tyr Leu Lys Lys Thr Gly Gln Leu
            260                 265                 270

<210> SEQ ID NO 4
<211> LENGTH: 51
<212> TYPE: PRT
<213> ORGANISM: artificial sequence
<220> FEATURE:
<223> OTHER INFORMATION: 2A peptide + N terminal part of capsid protein

<400> SEQUENCE: 4

Glu Gly Arg Gly Ser Leu Leu Thr Cys Gly Asp Val Glu Glu Asn Pro
1               5                   10                  15

Gly Pro Ser Gly Arg Lys Ala Gln Gly Lys Thr Leu Gly Val Asn Met
            20                  25                  30

Val Arg Arg Gly Val Arg Ser Leu Ser Asn Lys Ile Lys Gln Lys Thr
        35                  40                  45

Lys Gln Ile

<210> SEQ ID NO 5
<211> LENGTH: 806
<212> TYPE: DNA
<213> ORGANISM: Artificial Sequence
<220> FEATURE:
<223> OTHER INFORMATION: YF17D based constructs with hepatitis antigen

<400> SEQUENCE: 5

```
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
cggatccatg gacatcgacc cttataaaga atttggagct actgtggagt tactctcgtt     240
tttgccttct gacttctttc cttcagtacg agatcttcta gataccgcct cagctctgta     300
tcgggaagcc ttagagtctc ctgagcattg ttcacctcac catactgcac tcaggcaagc     360
aattctttgc tgggggaac  taatgactct agctacctgg gtgggtgtta atttggaaga     420
tccagcgtct agagacctag tagtcagtta tgtcaacact aatatgggcc taaagttcag     480
gcaactcttg tggtttcaca tttcttgtct cacttttgga agagaaacag ttatagagta     540
tttggtgtct ttcggagtgt ggattcgcac tcctccagct tatagaccac caaatgcccc     600
tatcctatca acacttccgg agactactgt tgttagacga cgaggcaggt ccgagggacg     660
cgggtccctg ctgacctgtg cgacgtgga  ggagaacccc ggtcctagcg ccgcaaagc      720
ccagggtaag acactgggcg tgaacatggt tcgtcgcggc gtccggtcct tgtcaaacaa     780
aataaaacaa aaaacaaaac aaattg                                         806
```

<210> SEQ ID NO 6
<211> LENGTH: 229
<212> TYPE: PRT
<213> ORGANISM: Artificial Sequence
<220> FEATURE:
<223> OTHER INFORMATION: YFV based construct with hepatitis antigen

<400> SEQUENCE: 6

```
Met Ser Gly Arg Lys Ala Gln Gly Lys Thr Leu Gly Val Asn Met Val
1               5                   10                  15

Arg Arg Gly Val Arg Gly Ser Met Asp Ile Asp Pro Tyr Lys Glu Phe
            20                  25                  30

Gly Ala Thr Val Glu Leu Leu Ser Phe Leu Pro Ser Asp Phe Phe Pro
        35                  40                  45

Ser Val Arg Asp Leu Leu Asp Thr Ala Ser Ala Leu Tyr Arg Glu Ala
    50                  55                  60

Leu Glu Ser Pro Glu His Cys Ser Pro His His Thr Ala Leu Arg Gln
65                  70                  75                  80

Ala Ile Leu Cys Trp Gly Glu Leu Met Thr Leu Ala Thr Trp Val Gly
                85                  90                  95

Val Asn Leu Glu Asp Pro Ala Ser Arg Asp Leu Val Val Ser Tyr Val
            100                 105                 110

Asn Thr Asn Met Gly Leu Lys Phe Arg Gln Leu Leu Trp Phe His Ile
        115                 120                 125

Ser Cys Leu Thr Phe Gly Arg Glu Thr Val Ile Glu Tyr Leu Val Ser
    130                 135                 140

Phe Gly Val Trp Ile Arg Thr Pro Pro Ala Tyr Arg Pro Pro Asn Ala
145                 150                 155                 160
```

```
Pro Ile Leu Ser Thr Leu Pro Glu Thr Thr Val Val Arg Arg Arg Gly
            165                 170                 175

Arg Ser Glu Gly Arg Gly Ser Leu Leu Thr Cys Gly Asp Val Glu Glu
            180                 185                 190

Asn Pro Gly Pro Ser Gly Arg Lys Ala Gln Gly Lys Thr Leu Gly Val
            195                 200                 205

Asn Met Val Arg Arg Gly Val Arg Ser Leu Ser Asn Lys Ile Lys Gln
            210                 215                 220

Lys Thr Lys Gln Ile
225

<210> SEQ ID NO 7
<211> LENGTH: 154
<212> TYPE: PRT
<213> ORGANISM: Artificial Sequence
<220> FEATURE:
<223> OTHER INFORMATION: Hepatis B antigen sequence

<400> SEQUENCE: 7

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
            50                  55                  60

Leu Met Asn Leu Ala Thr Trp Val Gly Gly Asn Leu Glu Asp Pro Ala
65              70                  75                  80

Ser Arg Glu Ala Val Val Ser Tyr Val Asn Val Asn Met Gly Leu Lys
            85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Gln Asn Ala Pro Ile Leu Ser Thr Leu Pro
            130                 135                 140

Glu Thr Thr Val Val Arg Arg Arg Gly Arg
145                 150

<210> SEQ ID NO 8
<211> LENGTH: 1429
<212> TYPE: DNA
<213> ORGANISM: Artificial Sequence
<220> FEATURE:
<223> OTHER INFORMATION: YFV based construct with ovalbumin

<400> SEQUENCE: 8
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
cggatccatg ggtagtatcg gggcagcctc catggagttc tgctttgacg tattcaaaga     240
gctcaaggtt catcatgcta acgaaaacat ttttattgc cccatcgcca taatgagtgc      300
tctggccatg tgtatcttg gggccaaaga ttcaacacgg acacagataa acaaagtagt      360
ccgcttcgac aaaattgcct gatttggcga ttctatcgaa gctcagtgcg ggacatccgt     420
```

```
gaatgtgcat agtagtctca gggatatcct caaccagata acaaaaccaa atgacgttta      480
ttctttagc  ctcgccagtc gcctttatgc cgaggaacgg tatcccattt tgccagagta      540
cttgcaatgt gtaaaagagt tgtaccgagg cgggctcgaa cccattaatt tccagacagc      600
agcagaccaa gcaagagagc ttataaatag ctgggtagaa tctcaaacta acggaattat      660
aagaaacgtg ctccaaccaa gttcagtgga ttctcagaca gccatggtcc ttgttaatgc      720
cattgttttc aaaggtcttt gggagaaagc atttaaagat gaggataccc aggctatgcc      780
ctttcgagta accgaacaag agagtaagcc cgtacaaatg atgtaccaga taggattgtt      840
tagagtcgcc tccatggcta gtgagaagat gaagattctg gagctcccct ttgccagcgg      900
tacaatgagc atgcttgtcc tgctccctga cgaggtgtca gggctcgaac aattggagag      960
cattatcaac ttcgagaaac tcacagaatg gactagtagc aatgtgatgg aggaaaggaa     1020
gattaaggta tatcttccac ggatgaaaat ggaagagaaa tacaatctca aagcgtact      1080
catggctatg ggaataacag atgtgttttc atccagcgcc aacttgagcg gcattagctc     1140
tgccgaaagt ctgaagattt cacaggccgt acatgccgcc cacgctgaaa taaatgaggc     1200
tggcagggaa gtagttggga gtgcagaggc tggcgtagat gctgccagcg tatccgagga     1260
gttccgagcc gatcacccct ttctcttttg tatcaaacat attgctacta atgcagtcct     1320
cttttcgt  cggtgtgtga gcccagaggg acgcgggtcc ctgctgacct gtggcgacgt     1380
ggaggagaac cccggtccta caaaataaaa caaaaaacaa aacaaattg                  1429
```

<210> SEQ ID NO 9
<211> LENGTH: 460
<212> TYPE: PRT
<213> ORGANISM: Artificial Sequence
<220> FEATURE:
<223> OTHER INFORMATION: YFV based construct with ovalbumin

<400> SEQUENCE: 9

```
Met Ser Gly Arg Lys Ala Gln Gly Lys Thr Leu Gly Val Asn Met Val
1               5                   10                  15

Arg Arg Gly Val Arg Gly Ser Met Gly Ser Ile Gly Ala Ala Ser Met
            20                  25                  30

Glu Phe Cys Phe Asp Val Phe Lys Glu Leu Lys Val His His Ala Asn
        35                  40                  45

Glu Asn Ile Phe Tyr Cys Pro Ile Ala Ile Met Ser Ala Leu Ala Met
    50                  55                  60

Val Tyr Leu Gly Ala Lys Asp Ser Thr Arg Thr Gln Ile Asn Lys Val
65                  70                  75                  80

Val Arg Phe Asp Lys Leu Pro Gly Phe Gly Asp Ser Ile Glu Ala Gln
                85                  90                  95

Cys Gly Thr Ser Val Asn Val His Ser Ser Leu Arg Asp Ile Leu Asn
            100                 105                 110

Gln Ile Thr Lys Pro Asn Asp Val Tyr Ser Phe Ser Leu Ala Ser Arg
        115                 120                 125

Leu Tyr Ala Glu Glu Arg Tyr Pro Ile Leu Pro Glu Tyr Leu Gln Cys
    130                 135                 140

Val Lys Glu Leu Tyr Arg Gly Gly Leu Glu Pro Ile Asn Phe Gln Thr
145                 150                 155                 160

Ala Ala Asp Gln Ala Arg Glu Leu Ile Asn Ser Trp Val Glu Ser Gln
                165                 170                 175

Thr Asn Gly Ile Ile Arg Asn Val Leu Gln Pro Ser Ser Val Asp Ser
```

```
                180                 185                 190
    Gln Thr Ala Met Val Leu Val Asn Ala Ile Val Phe Lys Gly Leu Trp
            195                 200                 205
    Glu Lys Ala Phe Lys Asp Glu Asp Thr Gln Ala Met Pro Phe Arg Val
            210                 215                 220
    Thr Glu Gln Glu Ser Lys Pro Val Gln Met Met Tyr Gln Ile Gly Leu
    225                 230                 235                 240
    Phe Arg Val Ala Ser Met Ala Ser Glu Lys Met Lys Ile Leu Glu Leu
                    245                 250                 255
    Pro Phe Ala Ser Gly Thr Met Ser Met Leu Val Leu Leu Pro Asp Glu
                    260                 265                 270
    Val Ser Gly Leu Glu Gln Leu Glu Ser Ile Ile Asn Phe Glu Lys Leu
                    275                 280                 285
    Thr Glu Trp Thr Ser Ser Asn Val Met Glu Glu Arg Lys Ile Lys Val
                    290                 295                 300
    Tyr Leu Pro Arg Met Lys Met Glu Glu Lys Tyr Asn Leu Thr Ser Val
    305                 310                 315                 320
    Leu Met Ala Met Gly Ile Thr Asp Val Phe Ser Ser Ser Ala Asn Leu
                    325                 330                 335
    Ser Gly Ile Ser Ser Ala Glu Ser Leu Lys Ile Ser Gln Ala Val His
                    340                 345                 350
    Ala Ala His Ala Glu Ile Asn Glu Ala Gly Arg Glu Val Val Gly Ser
                    355                 360                 365
    Ala Glu Ala Gly Val Asp Ala Ala Ser Val Ser Glu Glu Phe Arg Ala
                    370                 375                 380
    Asp His Pro Phe Leu Phe Cys Ile Lys His Ile Ala Thr Asn Ala Val
    385                 390                 395                 400
    Leu Phe Phe Gly Arg Cys Val Ser Pro Glu Arg Gly Ser Leu Leu
                    405                 410                 415
    Thr Cys Gly Asp Val Glu Glu Asn Pro Gly Pro Ser Gly Arg Lys Ala
                    420                 425                 430
    Gln Gly Lys Thr Leu Gly Val Asn Met Val Arg Arg Gly Val Arg Ser
                    435                 440                 445
    Leu Ser Asn Lys Ile Lys Gln Lys Thr Lys Gln Ile
                    450                 455                 460

<210> SEQ ID NO 10
<211> LENGTH: 386
<212> TYPE: PRT
<213> ORGANISM: Gallus gallus

<400> SEQUENCE: 10

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
                20                  25                  30

Ile Ala Ile Met Ser Ala Leu Ala Met Val Tyr Leu Gly Ala Lys Asp
            35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95
```

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
            115                 120                 125

Gly Leu Glu Pro Ile Asn Phe Gln Thr Ala Ala Asp Gln Ala Arg Glu
        130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385

<210> SEQ ID NO 11
<211> LENGTH: 1064
<212> TYPE: DNA
<213> ORGANISM: Artificial Sequence
<220> FEATURE:
<223> OTHER INFORMATION: YFV based construct with EBNA 1 antigen

<400> SEQUENCE: 11
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
cggatccggt agaaggccat ttttccaccc tgtaggggaa gccgattatt ttgaatacca     240
ccaagaaggt ggcccagatg gtgagcctga cgtgcccccg ggagcgatag gcagggccc      300 cgcagatgac ccaggagaag gcccaagcac tggaccccgg ggtcagggtg atggaggcag     360

```
gcgcaaaaaa ggagggtggt ttggaaagca tcgtggtcaa ggaggttcca acccgaaatt    420
tgagaacatt gcagaaggtt taagagctct cctggctagg agtcacgtag aaaggactac    480
cgacgaagga acttgggtcg ccggtgtgtt cgtatatgga ggtagtaaga cctcccttta    540
caacctaagg cgaggaactg cccttgctat tccacaatgt cgtcttacac cattgagtcg    600 tctcccctttt ggaatggccc ctggacccgg cccacaacct ggcccgctaa gggagtccat    660
tgtctgttat ttcatggtct ttttacaaac tcatatattt gctgaggttt tgaaggatgc    720
gattaaggac cttgttatga caaagcccgc tcctacctgc aatatcaggg tgactgtgtg    780
cagctttgac gatggagtag atttgcctcc ctggtttcca cctatggtgg aagggggctgc    840 cgcggagggt gatgacggag atgacggaga tgaaggaggt gatggagatg agggtgagga    900
agggcaggag gagggacgcg ggtccctgct gacctgtggc gacgtggagg agaacccccgg    960 tcctagcggc cgcaaagccc agggtaagac actgggcgtg aacatggttc gtcgcggcgt   1020
ccggtccttg tcaaacaaaa taaaacaaaa aacaaaacaa attg                    1064
```

<210> SEQ ID NO 12
<211> LENGTH: 315
<212> TYPE: PRT
<213> ORGANISM: Artificial Sequence
<220> FEATURE:
<223> OTHER INFORMATION: YVF based construct with EBNA1 antigen

<400> SEQUENCE: 12

```
Met Ser Gly Arg Lys Ala Gln Gly Lys Thr Leu Gly Val Asn Met Val
1               5                   10                  15

Arg Arg Gly Val Arg Gly Ser Gly Arg Arg Pro Phe Phe His Pro Val
            20                  25                  30

Gly Glu Ala Asp Tyr Phe Glu Tyr His Gln Glu Gly Gly Pro Asp Gly
        35                  40                  45

Glu Pro Asp Val Pro Pro Gly Ala Ile Glu Gln Gly Pro Ala Asp Asp
    50                  55                  60

Pro Gly Glu Gly Pro Ser Thr Gly Pro Arg Gly Gln Gly Asp Gly Gly
65                  70                  75                  80

Arg Arg Lys Lys Gly Gly Trp Phe Gly Lys His Arg Gly Gln Gly Gly
                85                  90                  95

Ser Asn Pro Lys Phe Glu Asn Ile Ala Glu Gly Leu Arg Ala Leu Leu
            100                 105                 110

Ala Arg Ser His Val Glu Arg Thr Thr Asp Glu Gly Thr Trp Val Ala
        115                 120                 125

Gly Val Phe Val Tyr Gly Gly Ser Lys Thr Ser Leu Tyr Asn Leu Arg
    130                 135                 140

Arg Gly Thr Ala Leu Ala Ile Pro Gln Cys Arg Leu Thr Pro Leu Ser
145                 150                 155                 160

Arg Leu Pro Phe Gly Met Ala Pro Gly Pro Gly Pro Gln Pro Gly Pro
                165                 170                 175

Leu Arg Glu Ser Ile Val Cys Tyr Phe Met Val Phe Leu Gln Thr His
            180                 185                 190

Ile Phe Ala Glu Val Leu Lys Asp Ala Ile Lys Asp Leu Val Met Thr
        195                 200                 205

Lys Pro Ala Pro Thr Cys Asn Ile Arg Val Thr Val Cys Ser Phe Asp
    210                 215                 220

Asp Gly Val Asp Leu Pro Pro Trp Phe Pro Pro Met Val Glu Gly Ala
225                 230                 235                 240
```

```
Ala Ala Glu Gly Asp Asp Gly Asp Gly Asp Glu Gly Gly Asp Gly
            245                 250                 255

Asp Glu Gly Glu Glu Gly Gln Glu Gly Arg Gly Ser Leu Leu Thr
        260                 265                 270

Cys Gly Asp Val Glu Glu Asn Pro Gly Pro Ser Gly Arg Lys Ala Gln
            275                 280                 285

Gly Lys Thr Leu Gly Val Asn Met Val Arg Gly Val Arg Ser Leu
        290                 295                 300

Ser Asn Lys Ile Lys Gln Lys Thr Lys Gln Ile
305                 310                 315
```

<210> SEQ ID NO 13
<211> LENGTH: 238
<212> TYPE: PRT
<213> ORGANISM: Artificial Sequence
<220> FEATURE:
<223> OTHER INFORMATION: EBNA1 antigen

<400> SEQUENCE: 13

```
Pro Phe Phe His Pro Val Gly Glu Ala Asp Tyr Phe Glu Tyr Leu Gln
1               5                   10                  15

Glu Gly Gly Pro Asp Gly Glu Pro Asp Val Pro Pro Gly Ala Ile Glu
            20                  25                  30

Gln Gly Pro Ala Asp Asp Pro Gly Glu Gly Pro Ser Thr Gly Pro Arg
        35                  40                  45

Gly Gln Gly Asp Gly Gly Arg Arg Lys Lys Gly Gly Trp Phe Gly Lys
    50                  55                  60

His Arg Gly Gln Gly Gly Ser Asn Pro Lys Phe Glu Asn Ile Ala Glu
65                  70                  75                  80

Gly Leu Arg Val Leu Leu Ala Arg Ser His Val Glu Arg Thr Thr Glu
                85                  90                  95

Glu Gly Thr Trp Val Ala Gly Val Phe Val Tyr Gly Gly Ser Lys Thr
            100                 105                 110

Ser Leu Tyr Asn Leu Arg Arg Gly Thr Ala Leu Ala Ile Pro Gln Cys
        115                 120                 125

Arg Leu Thr Pro Leu Ser Arg Leu Pro Phe Gly Met Ala Pro Gly Pro
    130                 135                 140

Gly Pro Gln Pro Gly Pro Leu Arg Glu Ser Ile Val Cys Tyr Phe Met
145                 150                 155                 160

Val Phe Leu Gln Thr His Ile Phe Ala Glu Val Leu Lys Asp Ala Ile
                165                 170                 175

Lys Asp Leu Val Met Thr Lys Pro Ala Pro Thr Cys Asn Ile Lys Val
            180                 185                 190

Thr Val Cys Ser Phe Asp Asp Gly Val Asp Leu Pro Pro Trp Phe Pro
        195                 200                 205

Pro Met Val Glu Gly Ala Ala Ala Glu Gly Asp Asp Gly Asp Asp Gly
    210                 215                 220

Asp Glu Gly Gly Asp Gly Asp Glu Gly Glu Glu Gly Gln Glu
225                 230                 235
```

<210> SEQ ID NO 14
<211> LENGTH: 63
<212> TYPE: DNA
<213> ORGANISM: Artificial Sequence
<220> FEATURE:
<223> OTHER INFORMATION: cDNA for YFV capsid nterminal fragment

<400> SEQUENCE: 14

```
atgtctggtc gtaaagctca gggaaaaacc ctgggcgtca atatggtacg acgaggagtt      60
cgc                                                                    63
```

<210> SEQ ID NO 15
<211> LENGTH: 60
<212> TYPE: DNA
<213> ORGANISM: Artificial Sequence
<220> FEATURE:
<223> OTHER INFORMATION: cDNA for capsid nterminal fragment

<400> SEQUENCE: 15

```
agcggccgca aagcccaggg taagacactg ggcgtgaaca tggttcgtcg cggcgtccgg      60
```

<210> SEQ ID NO 16
<211> LENGTH: 18
<212> TYPE: PRT
<213> ORGANISM: Thosea asigna

<400> SEQUENCE: 16

```
Glu Gly Arg Gly Ser Leu Leu Thr Cys Gly Asp Val Glu Glu Asn Pro
1               5                   10                  15

Gly Pro
```

<210> SEQ ID NO 17
<211> LENGTH: 12
<212> TYPE: PRT
<213> ORGANISM: Artificial Sequence
<220> FEATURE:
<223> OTHER INFORMATION: viral 2A cleaving peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 17

```
Leu Xaa Xaa Xaa Gly Asp Val Glu Xaa Pro Gly Pro
1               5                   10
```

<210> SEQ ID NO 18
<211> LENGTH: 13
<212> TYPE: PRT
<213> ORGANISM: Thosea asigna

<400> SEQUENCE: 18

```
Leu Leu Thr Cys Gly Asp Val Glu Glu Asn Pro Gly Pro
1               5                   10
```

<210> SEQ ID NO 19
<211> LENGTH: 56
<212> TYPE: DNA
<213> ORGANISM: Artificial Sequence
<220> FEATURE:
<223> OTHER INFORMATION: pcr primer

<400> SEQUENCE: 19

```
aagctcaggg aaaaaccctg gcgtcaata tggtacgacg aggagttcgc ggatcc           56
```

<210> SEQ ID NO 20
<211> LENGTH: 60
<212> TYPE: DNA
<213> ORGANISM: Artificial Sequence
<220> FEATURE:
<223> OTHER INFORMATION: pcr primer

<400> SEQUENCE: 20
gtgtcttacc ctgggctttg cggccgctag gaccggggtt ctcctccacg tcgccacagg    60

<210> SEQ ID NO 21
<211> LENGTH: 60
<212> TYPE: DNA
<213> ORGANISM: Artificial Sequence
<220> FEATURE:
<223> OTHER INFORMATION: pcr primer

<400> SEQUENCE: 21
gtcaatatgg tacgacgagg agttcgcgga tccgtttaaa cctcgtcccc gccgggtcac    60

<210> SEQ ID NO 22
<211> LENGTH: 60
<212> TYPE: DNA
<213> ORGANISM: Artificial Sequence
<220> FEATURE:
<223> OTHER INFORMATION: pcr primer

<400> SEQUENCE: 22
gtcgccacag gtcagcaggg acccgcgtcc ctcgtttaaa cagtatagcg accagcattc    60

<210> SEQ ID NO 23
<211> LENGTH: 60
<212> TYPE: DNA
<213> ORGANISM: Artificial Sequence
<220> FEATURE:
<223> OTHER INFORMATION: pcr primer

<400> SEQUENCE: 23
cagaacatgt ctggtcgtaa agctcaggga aaaaccctgg gcgtcaatat ggtacgacga    60

<210> SEQ ID NO 24
<211> LENGTH: 60
<212> TYPE: DNA
<213> ORGANISM: Artificial Sequence
<220> FEATURE:
<223> OTHER INFORMATION: pcr primer

<400> SEQUENCE: 24
accctgggct tgcggccgc taggaccggg gttctcctcc acgtcgccac aggtcagcag    60

<210> SEQ ID NO 25
<211> LENGTH: 60
<212> TYPE: DNA
<213> ORGANISM: Artificial Sequence
<220> FEATURE:
<223> OTHER INFORMATION: pcr primer

<400> SEQUENCE: 25
ccggacgccg cgacgaacca tgttcacgcc cagtgtctta ccctgggctt tgcggccgct    60

<210> SEQ ID NO 26
<211> LENGTH: 60
<212> TYPE: DNA
<213> ORGANISM: Artificial Sequence
<220> FEATURE:
<223> OTHER INFORMATION: pcr primer

<400> SEQUENCE: 26
cctgggcgtc aatatggtac gacgaggagt tcgcggatcc atggacatcg acccttataa    60

<210> SEQ ID NO 27
<211> LENGTH: 60
<212> TYPE: DNA
<213> ORGANISM: Artificial Sequence
<220> FEATURE:
<223> OTHER INFORMATION: pcr primer

<400> SEQUENCE: 27
cctccacgtc gccacaggtc agcagggacc cgcgtccctc cgcgagggcc tttccctcgg    60

<210> SEQ ID NO 28
<211> LENGTH: 60
<212> TYPE: DNA
<213> ORGANISM: Artificial Sequence
<220> FEATURE:
<223> OTHER INFORMATION: pcr primer

<400> SEQUENCE: 28
gtcttaccct gggctttgcg gccgctagga ccggggttct cctccacgtc gccacaggtc    60

<210> SEQ ID NO 29
<211> LENGTH: 60
<212> TYPE: DNA
<213> ORGANISM: Artificial Sequence
<220> FEATURE:
<223> OTHER INFORMATION: pcr primer

<400> SEQUENCE: 29
tggaggagaa ccccggtcct agcggccgca aagcccaggg taagacactg ggcgtgaaca    60

<210> SEQ ID NO 30
<211> LENGTH: 60
<212> TYPE: DNA
<213> ORGANISM: Artificial Sequence
<220> FEATURE:
<223> OTHER INFORMATION: pcr primer

<400> SEQUENCE: 30
taagacactg ggcgtgaaca tggttcgtcg cggcgtccgg tccttgtcaa acaaaataaa    60

<210> SEQ ID NO 31
<211> LENGTH: 60
<212> TYPE: DNA
<213> ORGANISM: Artificial Sequence
<220> FEATURE:
<223> OTHER INFORMATION: pcr primer

<400> SEQUENCE: 31
tgacgcccag ggttttccc tgagctttac gaccagacat gttctggtca gttctctgct    60

<210> SEQ ID NO 32
<211> LENGTH: 60
<212> TYPE: DNA
<213> ORGANISM: Artificial Sequence
<220> FEATURE:
<223> OTHER INFORMATION: pcr primer

<400> SEQUENCE: 32
tcgatgtcca tggatccgcg aactcctcgt cgtaccatat tgacgcccag ggttttccc    60

<210> SEQ ID NO 33
<211> LENGTH: 57
<212> TYPE: DNA
<213> ORGANISM: Artificial Sequence
<220> FEATURE:
<223> OTHER INFORMATION: pcr primer

```
<400> SEQUENCE: 33
tggattaatt ttaatcgttc gttgagcgat tagcagagaa ctgaccagaa catgtct      57

<210> SEQ ID NO 34
<211> LENGTH: 57
<212> TYPE: DNA
<213> ORGANISM: Artificial Sequence
<220> FEATURE:
<223> OTHER INFORMATION: pcr primer

<400> SEQUENCE: 34
cctccacgtc gccacaggtc agcagggacc cgcgtccctc ggacctgcct cgtcgtc      57

<210> SEQ ID NO 35
<211> LENGTH: 60
<212> TYPE: DNA
<213> ORGANISM: Artificial Sequence
<220> FEATURE:
<223> OTHER INFORMATION: pcr primer

<400> SEQUENCE: 35
tgtttccaat tgtttttgtt ttttgtttta ttttgtttga caaggaccgg acgccgcgac   60

<210> SEQ ID NO 36
<211> LENGTH: 60
<212> TYPE: DNA
<213> ORGANISM: Artificial Sequence
<220> FEATURE:
<223> OTHER INFORMATION: pcr primer

<400> SEQUENCE: 36
gggcgtcaat atggtacgac gaggagttcg cggatccatg ggtagaaggc catttttcca   60

<210> SEQ ID NO 37
<211> LENGTH: 60
<212> TYPE: DNA
<213> ORGANISM: Artificial Sequence
<220> FEATURE:
<223> OTHER INFORMATION: pcr primer

<400> SEQUENCE: 37
cctccacgtc gccacaggtc agcagggacc cgcgtccctc ctcctgccct tcctcaccct   60

<210> SEQ ID NO 38
<211> LENGTH: 24
<212> TYPE: PRT
<213> ORGANISM: Foot-and-mouth disease virus

<400> SEQUENCE: 38

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 39
<211> LENGTH: 19
<212> TYPE: PRT
<213> ORGANISM: Porcine teschovirus-1

<400> SEQUENCE: 39

Ala Thr Asn Phe Ser Leu Leu Lys Gln Ala Gly Asp Val Glu Glu Asn
1               5                   10                  15

Pro Gly Pro
```

<210> SEQ ID NO 40
<211> LENGTH: 20
<212> TYPE: PRT
<213> ORGANISM: equine rhinitis A virus

<400> SEQUENCE: 40

Gln Cys Thr Asn Tyr Ala Leu Leu Lys Leu Ala Gly Asp Val Glu Ser
1               5                   10                  15

Asn Pro Gly Pro
            20

<210> SEQ ID NO 41
<211> LENGTH: 29
<212> TYPE: PRT
<213> ORGANISM: Artificial Sequence
<220> FEATURE:
<223> OTHER INFORMATION: Yellow fever capsid fragment + Hbc fragment

<400> SEQUENCE: 41

Met Ser Gly Arg Lys Ala Gln Gly Lys Thr Leu Gly Val Asn Met Val
1               5                   10                  15

Arg Arg Gly Val Arg Gly Ser Met Asp Ile Asp Pro Tyr
            20                  25

<210> SEQ ID NO 42
<211> LENGTH: 30
<212> TYPE: PRT
<213> ORGANISM: Artificial Sequence
<220> FEATURE:
<223> OTHER INFORMATION: Hbc fragment - T2A peptide - Yeloow fever
      fragment

<400> SEQUENCE: 42

Arg Arg Arg Gly Arg Ser Glu Gly Arg Gly Ser Leu Leu Thr Cys Gly
1               5                   10                  15

Asp Val Glu Glu Asn Pro Gly Pro Ser Gly Arg Lys Ala Gln
            20                  25                  30

<210> SEQ ID NO 43
<211> LENGTH: 63
<212> TYPE: DNA
<213> ORGANISM: Yellow fever virus

<400> SEQUENCE: 43
atgtctggtc gtaaagctca gggaaaaacc ctgggcgtca atatggtacg acgaggagtt      60
cgc                                                                   63

<210> SEQ ID NO 44
<211> LENGTH: 58
<212> TYPE: DNA
<213> ORGANISM: Artificial Sequence
<220> FEATURE:
<223> OTHER INFORMATION: codon modified YFV capsid

<400> SEQUENCE: 44
cggccgcaaa gcccagggta agacactggg cgtgaacatg gttcgtcgcg gcgtccgg        58

<210> SEQ ID NO 45
<211> LENGTH: 21
<212> TYPE: PRT
<213> ORGANISM: Yellow fever virus

<400> SEQUENCE: 45

```
Met Ser Gly Arg Lys Ala Gln Gly Lys Thr Leu Gly Val Asn Met Val
1               5                   10                  15

Arg Arg Gly Val Arg
            20

<210> SEQ ID NO 46
<211> LENGTH: 8
<212> TYPE: PRT
<213> ORGANISM: Artificial Sequence
<220> FEATURE:
<223> OTHER INFORMATION: 2A peptide consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 46

Asp Xaa Glu Xaa Asn Pro Gly Pro
1               5

<210> SEQ ID NO 47
<211> LENGTH: 4
<212> TYPE: PRT
<213> ORGANISM: Artificial Sequence
<220> FEATURE:
<223> OTHER INFORMATION: 2A cleavage site

<400> SEQUENCE: 47

Asn Pro Gly Pro
1

<210> SEQ ID NO 48
<211> LENGTH: 5
<212> TYPE: PRT
<213> ORGANISM: Artificial Sequence
<220> FEATURE:
<223> OTHER INFORMATION: 2A cleavage site

<400> SEQUENCE: 48

Asn Pro Gly Pro Ser
1               5
```

LIVE-ATTENUATED FLAVIRUSES WITH HETEROLOGOUS ANTIGENS

BACKGROUND OF THE INVENTION

Hepatitis B virus (HBV) is the causative agent of hepatitis B, a liver disease that can evolve to chronicity. Complications of chronic hepatitis B include liver cirrhosis and hepatocellular carcinoma or liver cancer. An estimated 240 million people, mainly in Asia and Africa, are chronically infected with HBV, with more than 686.000 people dying every year due to complications related to chronic HBV infection. HBV is a member of the Hepadnaviridae, a family of retrotranscribing viruses with partially double-stranded genomic DNA. It is most commonly transmitted perinatally from an infected mother, or horizontally through unprotected sexual activities or intravenous drug use.

Upon infection of a hepatocyte by HBV, the HBV nucleocapsid is transported to the nucleus. There, the genetic material is repaired and retained as a mini-chromosome (cccDNA) in the nucleus of the cell where it functions as a reservoir.

Most patients control an acute infection efficiently without the appearance of any evident clinical symptoms. However, 5-10% of infected adults (and >90% of infected neonates) are unable to clear the virus and develop chronic hepatitis B. In those who clear the virus, vigorous and multispecific CD4 and CD8 T-cell responses of the Th1 profile (production of IFN-γ) are detected The CD4 T-cell response that is specific for the HBV nucleocapsid protein [also called HBV core antigen (HBcAg or HBc)] is important in HBV control since this stimulates the activation of CD8 T-cells [Jung et al. (1995) *J. Virol.* 69, 3358-3368]. In fact, CD8 T-cells, (or CTLs) are the main cellular subset responsible for resolution of the infection as they clear HBV-infected hepatocytes through cytolytic and non-cytolytic mechanisms. In those who do not resolve the infection and develop chronic hepatitis B, the responses are weaker. Indeed, it has been demonstrated that the level of HBV-specific CTLs is correlated to HBV control [Thimme et al. (2003) *J. Virol.* 77, 68-76].

The restoration of a strong CTL response is the main goal of a therapeutic HBV vaccine. Such vaccine is urgently awaited so as to be able to cure millions of people with chronic hepatitis B. The yellow fever vaccine (strain 17D) is one of the safest and most effective vaccines currently available. About 99% of those vaccinated (after a single dose) develop life-long immunity within days to weeks. The vaccine came into use in 1938 and since then over 600 million doses have been dispensed. It is important to note that the YFV17D vaccine does not only induce potent neutralizing antibodies but also (i) strong and broadly directed CD8+ T-cell responses, (ii) exceptionally strong memory T-cell responses as well as (iii) a potent activation of the innate immune system, especially of dendritic cells. Such characteristics may provide the ideal context for the construction therapeutic vaccines against chronic infections such as those caused by the hepatitis B virus.

Attempts have been made to clone antigens upstream of a yellow fever to obtain a fusion protein, whereby the antigen is released from the viral protein, using a protease signal peptide and an ubiquitin cleavage site [Schoggins et al. (2012) *Proc NatlAcadSci USA.* 109, 14610-14615.].

However as indicated in the review article of Bonaldo et al. (2014) *Hum. Vaccine. Immunother* 10, 1256-1265). such constructs lose the heterologous genes after a few passages. Alternative constructs are required to overcome the genetic instability.

SUMMARY OF THE INVENTION

The invention relates to polynucleotides comprising the sequence of a Yellow Fever virus wherein the nucleotide sequence encoding said Yellow Fever virus is preceded by an N terminal part of the yellow fever virus Capsid protein followed by a T cell antigen, or a part thereof comprising a T cell antigen, and the sequence encoding for the *Thosea asigna* 2A peptide.

Typically the nucleotide sequence of the N terminal part of the capsid gene has one or more synonymous codons compared with the corresponding sequence in the full length yellow fever virus sequence.

In an embodiment, the terminal part of the Yellow Fever virus capsid encodes for a peptide consisting of the sequence MSGRKAQGKTLGVNMVRRGVR (SEQ ID NO:2).

In an embodiment, the *Thosea asigna* 2A peptide has the sequence EGRGSLLTCGDVEENPGP (SEQ ID NO:16).

In an embodiment, the amino acid C terminal of the T2A peptide is Gly, Ala, Ser or Thr.

In an embodiment wherein the codon usage of the antigen is adapted for expression in bacteria.

In an embodiment the sequences with synonymous codons are:
atgtctggtcgtaaagctcagggaaaaaccctgggcgtcaatatggtacgacgaggagttcgc (SEQ ID NO: 14)
and
agcggccgcaaagcccagggtaagacactgggcgtgaacatggttcgtcgcggcgtccgg. (SEQ ID NO: 15).

In an embodiment, the Yellow Fever virus is the YF 17D attenuated virus.

In an embodiment, the polynucleotide is an Bacterial Artificial Chromosome.

In an embodiment, the BAC comprises an inducible bacterial ori sequence for amplification of said BAC to more than 10 copies per bacterial cell, and a viral expression cassette comprising a cDNA of said polynucleotide and comprising cis-regulatory elements for transcription of said viral cDNA in mammalian cells and for processing of the transcribed RNA into infectious RNA virus.

In an embodiment, said T cell antigen is selected from the group consisting of the core antigen of HBC, OVA and EBNA1, namely the encoded T cell antigen comprises the amino acid sequence of SEQ ID NO:3, or a fragment thereof comprising a T cell epitope, the encoded T cell antigen comprises the amino acid sequence of SEQ ID NO:7 or a fragment thereof comprising a T cell epitope, the encoded T cell antigen comprises the amino acid sequence of SEQ ID NO:10 or a fragment thereof comprising a T cell epitope; the encoded T cell antigen compromises the amino acid sequence of SEQ ID NO:13.

Such polynucleotides can be used as a vaccine, more particular for use as a vaccine in the prevention of an infection caused by said T cell antigen or partial T cell epitope. Furthermore, the above polynucleotides can be used as a vaccine in the simultaneous prevention of an infection caused by said T cell antigen or partial T cell epitope and of a Yellow Fever infection.

Herein disclosed are methods of preparing a vaccine against a T cell antigen, comprising the steps of:

(a) providing a BAC which comprises an inducible bacterial ori sequence for amplification of said BAC to more than 10 copies per bacterial cell, and a viral expression cassette comprising a cDNA of a polynucleotide as described above, and comprising cis-regulatory elements for transcription of said viral cDNA in mammalian cells and for processing of the transcribed RNA into infectious RNA virus (b) transfecting mammalian cells with the BAC of step (a)

(c) validating replicated virus of the transfected cells of step (b) for virulence and the capacity of generating antibodies against said T cell antigen, cloning the virus validated in step (c) into a vector, formulating the vector into a vaccine formulation.

Herein the vector is a BAC, can comprises an inducible bacterial ori sequence for amplification of said BAC to more than 10 copies per bacterial cell.

The present invention is equally applicable to other flaviviruses wherein T cell antigens are cloned N terminal of the capsid protein.

The present invention is equally applicable to chimeric yellow fever strains wherein the prME genes of the YFV are replaced by those of other flaviviruses such as Japanese Encephalitis or Dengue.

The invention is further summarized in the following statements:

1. A polynucleotide comprising the sequence of a flavivirus characterized in that the nucleotide sequence encoding said flavivirus is preceded by a sequence encoding:
   a part of a flavivirus Capsid protein comprising or consisting of the N terminal part of the flavivirus Capsid protein,
   an immunogenic protein, or a part thereof comprising an immunogenic peptide, and
   a 2A cleaving peptide.

For the purpose of vaccination, these flavivirusses are typically life infectious attenuated viruses.

2. The polynucleotide according to statement 1, wherein the part of the flavivirus Capsid protein comprises or consists of the 21 N terminal amino acids of the flavivirus Capsid protein.

The embodiment of 21 AA is based on the examples performed with YFV but may differ depending of the type of flavivirus and can be as short as 16 amino acids for Japanese Encephalitis virus.

Apart from the minimal essential N terminus of 16 to 21 amino acids, depending from the flavivirus considered, the chimeric virus may comprise prior the site of insertion a further part of the capsid protein, such that the N terminal fragment of the capsid may have a length of 25, 30, 35, 40 or 50 amino acids, since a Dengue virus constructs with an N terminal fragment of 34 amino acids have been described (Fischl & Bartenschlager (2013) Methods Mol. Biol. 1030, 205-219.

3. The polynucleotide according to statement 1 or 2, wherein the nucleotide sequence encoding the N terminal part of the capsid gene has one or more synonymous codons compared with the corresponding sequence in the full length viral sequence.

4. The polynucleotide according to statement 1, 2, or 3 wherein the flavivirus is yellow fever virus.

5. The polynucleotide according to any one of statements 1 to 4, where the terminal part of the Yellow Fever virus capsid consist of the sequence MSGRKAQGKTLGVNMVRRGVR (SEQ ID NO:2).

6. The polynucleotide according to any one of statements 1 to 5, wherein the 2A cleaving peptide comprises the sequence DXEXNPGP [SEQ ID NO:46].

7. The polynucleotide according to any one of statements 1 to 5, wherein the 2A cleaving peptide comprises the sequence LxxxGDVExPGP [SEQ ID NO:17].

8. The polynucleotide according to any one of statements 1 to 7, wherein the 2A cleaving peptide comprises the sequence LLTCGDVEENPGP [SEQ ID NO:18].

9. The polynucleotide according to any one of statements 1 to 8, wherein the 2A cleaving peptide is the *Thosea asigna* 2A peptide with amino acid sequence EGRGSLLTCGDVEENPGP (SEQ ID NO:16).

10. The polynucleotide according to any one of statements 1 to 9, wherein the amino acid C terminal of the 2A cleaving peptide is Gly, Ala, Ser or Thr.

11. The polynucleotide according to any one of statements 1 to 10, wherein the immunogenic protein is a T cell antigen and the immunogenic fragment thereof comprises a T cell epitope.

12. The polynucleotide according to any one of statements 1 to 11, wherein the nucleotide sequence encoding the capsid protein 5' of the sequence encoding said immunogenic protein or fragment thereof has the nucleotide sequence of the wild type flavivirus.

13. The polynucleotide according to any one of statements 1 to 11, wherein the codon usage of the immunogenic protein of immunogenic fragment thereof is adapted for expression in bacteria.

14. The polynucleotide according to any one of statements 1 to 12, wherein the sequences with synonymous codons are:
atgtctggtcgtaaagctcagggaaaaaccctgggcgtcaatatggtacgacgag-gagttcgc (SEQ ID NO: 14)
and
agcggccgcaaagcccagggtaagacactgggcgtgaa-catggttcgtcgcggcgtccgg (SEQ ID NO:15).

15. The polynucleotide according to any one of statements 1 to 14, wherein the Yellow Fever virus is the YF 17D attenuated virus.

16. The polynucleotide according to any one of statements 1 to 15, which is an Bacterial Artificial Chromosome.

17. The polynucleotide according to statement 16, wherein the BAC comprises an inducible bacterial ori sequence for amplification of said BAC to more than 10 copies per bacterial cell, and a viral expression cassette comprising a cDNA of said polynucleotide and comprising cis-regulatory elements for transcription of said viral cDNA in mammalian cells and for processing of the transcribed RNA into infectious RNA virus.

18. The polynucleotide according to any one of statements 1 to 17 wherein said T cell antigen is selected from the group consisting of the core antigen of HBC, OVA and EBNA1.

19. The polynucleotide according to any one of statements 1 to 18, wherein the encoded T cell antigen comprises the amino acid sequence of SEQ ID NO:3, or a fragment thereof comprising a T cell epitope.

20. The polynucleotide according to any one of statements 1 to 18, wherein the encoded T cell antigen comprises the amino acid sequence of SEQ ID NO:7 or a fragment thereof comprising a T cell epitope.

21. The polynucleotide according to any one of statements 1 to 18, wherein the encoded T cell antigen comprises the amino acid sequence of SEQ ID NO:10 or a fragment thereof comprising a T cell epitope.

22. The polynucleotide according to any one of statements 1 to 18, wherein the encoded T cell antigen compromises the amino acid sequence of SEQ ID NO:13.

23. A flavivirus fusion construct characterized in that the flavivirus is preceded at its aminoterminus by:
a part of a flavivirus Capsid protein comprising or consisting of the N terminal part of the flavivirus Capsid protein, an immunogenic protein, or a part thereof comprising an immunogenic peptide, and
a 2A cleaving peptide.

For the purpose of vaccination, these flaviviruses are typically life infectious attenuated viruses.

24. A flavivirus fusion construct to statement 23, wherein the part of the flavivirus Capsid protein comprises or consists of the 21 N terminal amino acids of the flavivirus Capsid protein.

25. The flavivirus fusion construct according to statement 23 or 24, wherein the flavivirus is yellow fever virus.

26. The flavivirus fusion construct statements 23, 24 or 25, where the terminal part of the Yellow Fever virus capsid consists of the sequence MSGRKAQGKTLGVNMVRRGVR (SEQ ID NO:2).

27. The polynucleotide according to any one of statements 23 to 25, wherein the 2A cleaving peptide comprises the sequence DXEXNPGP [SEQ ID NO:46].

28. The flavivirus fusion construct according to any one of statements 23 to 26, wherein the 2A cleaving peptide comprises the sequence LxxxGDVExPGP [SEQ ID NO: 17]

29. The flavivirus fusion construct according to any one of statements 23 to 28, wherein the 2A cleaving peptide comprises the sequence LLTCGDVEENPGP [SEQ ID NO: 18].

30 The flavivirus fusion construct according to any one of statements 23 to 28, wherein the 2A cleaving peptide is the *Thosea asigna* 2A peptide with amino acid sequence EGRGSLLTCGDVEENPGP (SEQ ID NO:16).

31. The flavivirus fusion construct according to any one of statements 23 to 30, wherein the amino acid C terminal of the 2A cleaving peptide is Gly, Ala, Ser or Thr.

32. The flavivirus fusion construct polynucleotide according to any one of statements 23 to 31, wherein the immunogenic protein is a T cell antigen and the immunogenic fragment thereof comprises a T cell epitope.

33. The flavivirus fusion construct according to any one of statements 23 to 32, wherein the Yellow Fever virus is the YF 17D attenuated virus.

34. The flavivirus fusion construct according to any one of statements 23 to 32, wherein the immunogenic protein is selected from the group consisting of the core antigen of HBC, OVA and EBNA1.

35. The flavivirus fusion construct according to any one of statements 23 to 32, wherein the HBC antigen comprises the amino acid sequence of SEQ ID NO:7, or a fragment thereof comprising a T cell epitope.

36. The polynucleotide according to any one of statements 1 to 22, for use as a vaccine.

37. The polynucleotide for use as a vaccine according to statement 36, in the prevention of an infection caused by said immunogenic protein or immunogenic peptide fragment thereof.

38. The polynucleotide for use as a vaccine according to statement 36, in the simultaneous prevention of an infection caused by said immunogenic protein or immunogenic peptide fragment thereof and of a flavivirus infection.

39. The flavivirus fusion construct according to any one of statements 23 to 35, for use as a vaccine.

40. The flavivirus fusion construct for use as a vaccine according to statement 39, in the prevention of an infection caused by said immunogenic protein or immunogenic peptide fragment thereof.

41. The flavivirus fusion construct for use as a vaccine according to statement 40, the simultaneous prevention of an infection caused by said immunogenic protein or immunogenic peptide fragment thereof and of a flavivirus infection.

42. The flavivirus fusion construct for use as a vaccine according to statement 40, in the simultaneous prevention of an infection caused by said T cell antigen or partial T cell epitope and of a Yellow Fever infection.

43. A pharmaceutical comprising a polynucleotide in accordance with any one of statements 1 to 22, and a pharmaceutical acceptable carrier.

44. A pharmaceutical comprising a flavivirus fusion construct in accordance with any one of statements 23 to 35, and a pharmaceutical acceptable carrier.

45. A method of preparing a vaccine against a immunogenic protein or peptide fragment thereof, comprising the steps of:
(a) providing a BAC which comprises an inducible bacterial ori sequence for amplification of said BAC to more than 10 copies per bacterial cell, and a viral expression cassette comprising a cDNA of a polynucleotide according to any one of statements 1 to 22, and comprising cis-regulatory elements for transcription of said cDNA in mammalian cells and for processing of the transcribed RNA into infectious RNA virus
(b) transfecting mammalian cells with the BAC of step (a)
(c) validating replicated virus of the transfected cells of step (b) for virulence and the capacity of generating antibodies against said T cell antigen, cloning the virus validated in step (c) into a vector, formulating the vector into a vaccine formulation.

46. The method according to statement 45, wherein the vector is a BAC, which comprises an inducible bacterial ori sequence for amplification of said BAC to more than 10 copies per bacterial cell.

47. A method of provoking an immune response to an immunogenic protein, comprising the step of administering an effective amount of a polynucleotide in accordance with any one of statements 1 to 22, or a flavivirus fusion construct in accordance with any one of statements 23 to 35.

DETAILED DESCRIPTION

FIG. 1: Detail of polyprotein of YFV17D/HBc. The first 155 amino acids of HBc, serotype ayw are preceded upstream of the YFV17D capsid (amino acids 1-21) and followed downstream by the *Thosea asigna* 2A peptide and the full-length YFV17D polyprotein, including the capsid protein.

Figure 2:
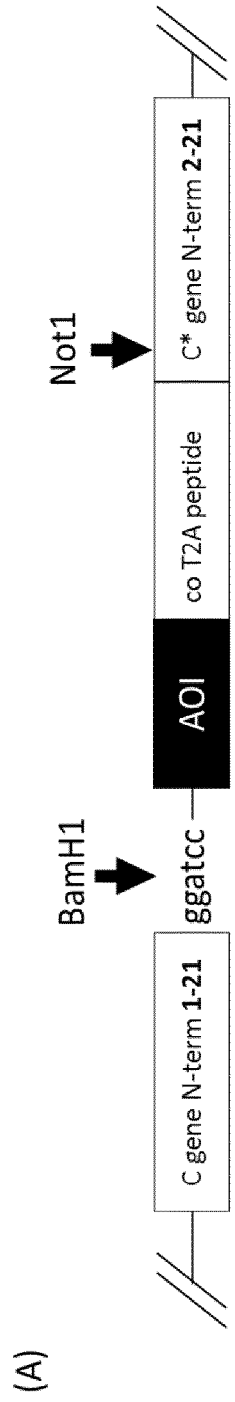

FIG. 2: shows a schematic map of cDNA constructs of the present invention. The Antigen Of Interest (AOI; e.g. HBV core antigen) is inserted as translational fusion to the first 21 N-terminal codons of the C gene in the YFV 17D ORF (C gene N-term 1-21) following an newly introduced in-frame BamH1 restriction endonuclease site. The AOI is fused C-terminally to a codon-optimized *Thosea asigna* virus 2A 'cleaving' peptide (co T2A peptide) followed by a codon modified repeat of the 2-21 codons of the YFV 17D C-gene (C* gene N-term 2-21). Downstream of latter cDNA element the construct continues as genuine YFV 17D cDNA.

Sequence alignment of first 21 codons of the wild-type YFV 17D ORF (wt-YF17D C gene N-term) with the modified repeat thereof (Modified repeat) encoding for C* gene N-term 2-21 in (A). Small letters indicate nucleotide changes introduced relative to wt-YF17D C gene N-term. A newly introduced Not1 restriction endonuclease site (gcGGcCGc) is highlighted in Black.

Figure 3:
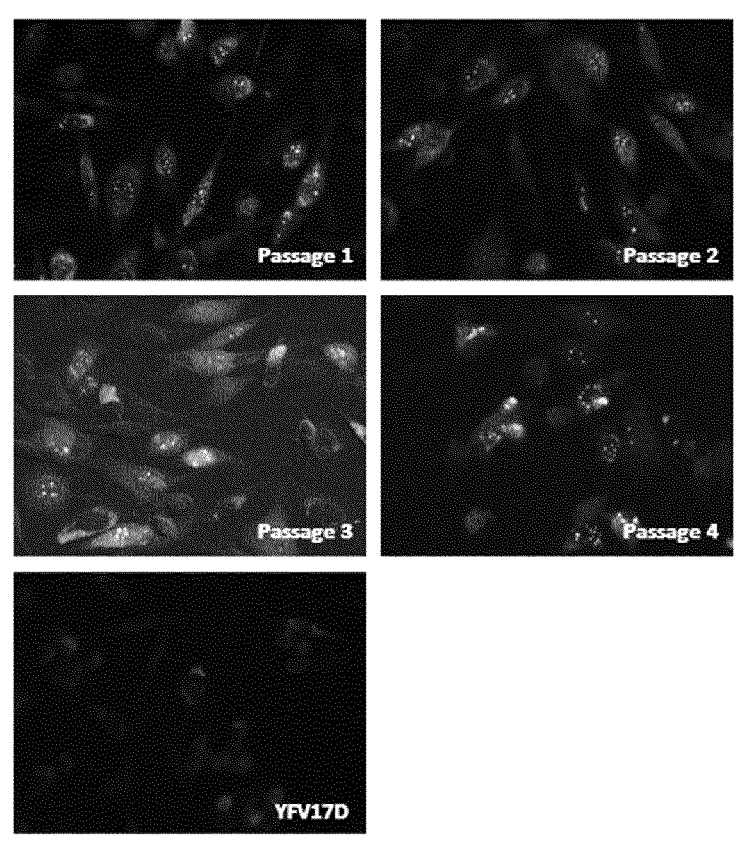

FIG. 3: Immunofluorescence imaging of YFV17D/HBc passages and YFV17D. Red: HBc, Green: YFV antigens.

Figures 4, 5:
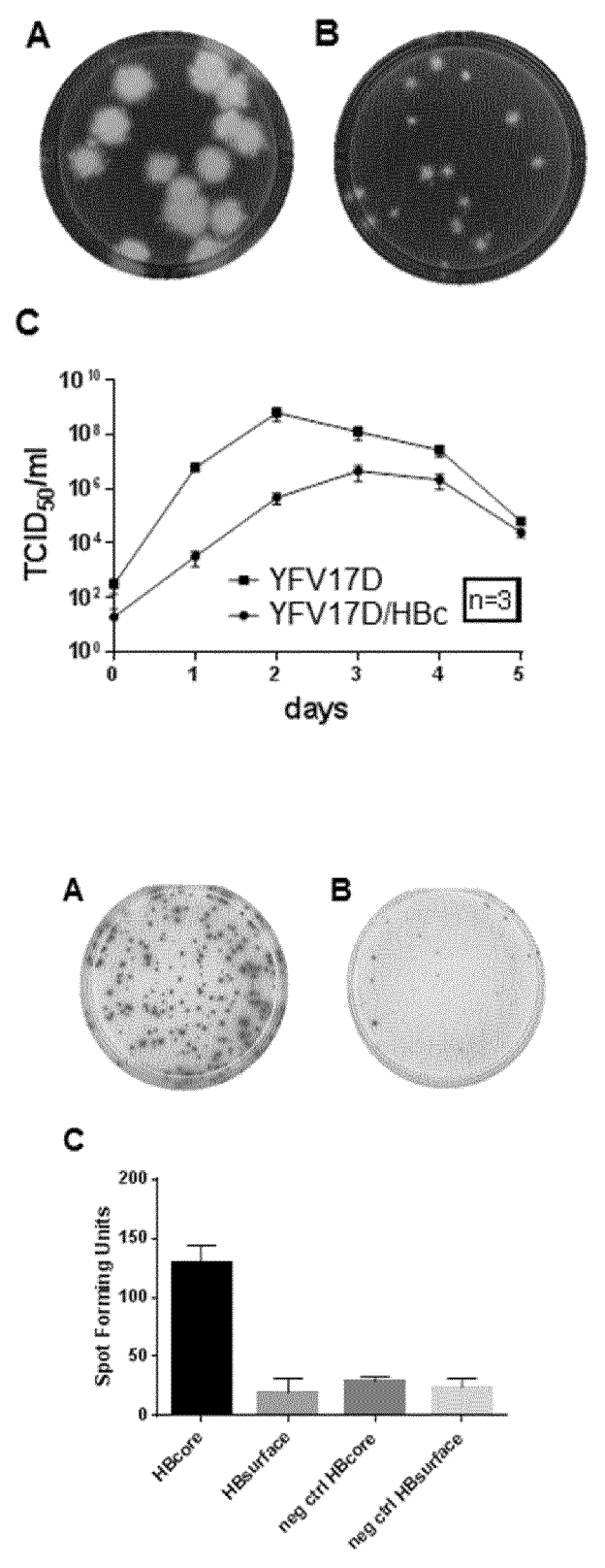

FIG. 4: in vitro characterization of YFV17D/HBc. A) YFV17D plaques, B) YFV17D/HBc, C) growth curves of YFV17D and YFV17D/HBc.

FIG. 5: mouse IFN-γ ELISPOT. Splenocytes isolated from YFV17D/HBc-immunized AG129 mice were stimulated with peptides derived from HBcAg (A) and HBsAg (B). Spot forming units (SFU) for splenocytes of YFV17D/HBc and Chimerivax-JE immunized mice stimulated with HBcAg and HBsAg (C).

Figures 6, 7:
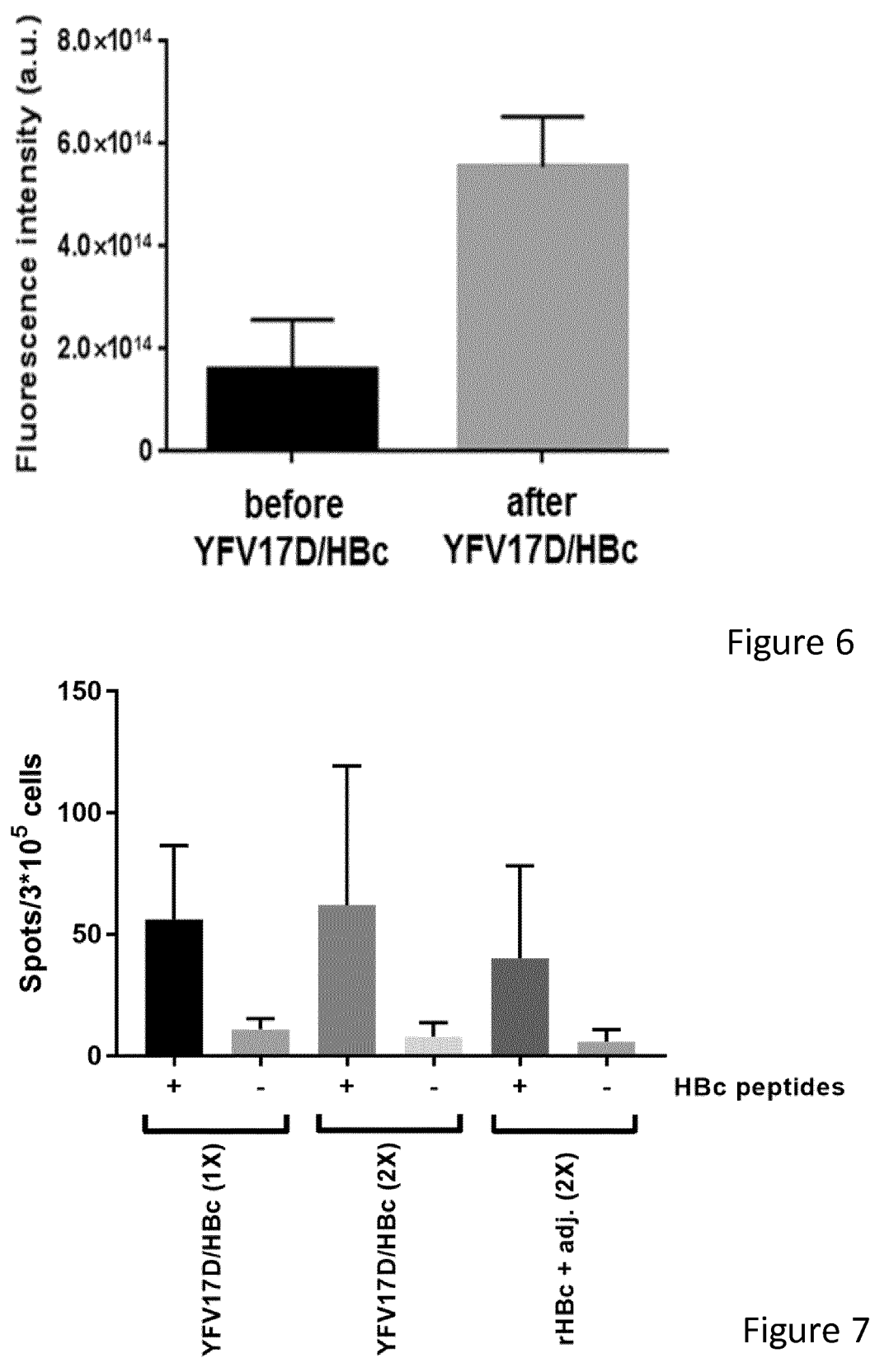

FIG. 6: Fluorescence intensities from immunofluorescence assay with serum collected before and after YFV17D/HBc immunization.

FIG. 7: mouse IFN-γ ELISPOT. SFU for splenocytes ($3\times10^5$) isolated from AG129 mice immunized once (1×) or twice (2×) with YFV17D/HBc or twice with rHBc+Quil-A®, stimulated with peptides derived from HBcAg (+) or not stimulated (−).

Figure 8:
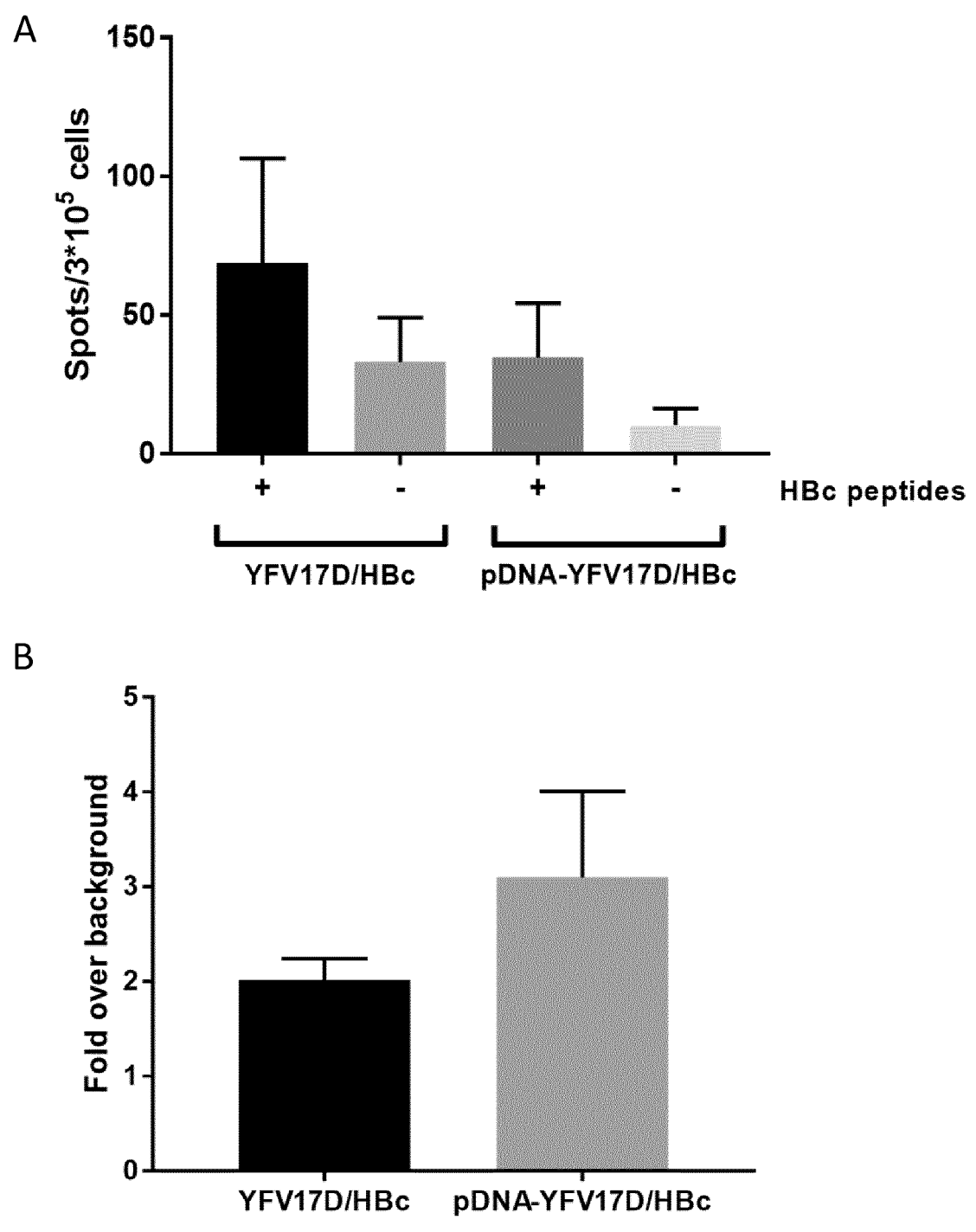

FIG. 8: mouse IFN-γ ELISPOT. A) SFU for splenocytes ($3\times10^5$) isolated from AG129 mice immunized with YFV17D/HBc or with pDNA-YFV17D/HBc and PEI, stimulated with peptides derived from HBcAg (+) or not stimulated (−). B) fold over background (HBc peptide-stimulated over non-stimulated) for splenocytes isolated from AG129 mice immunized with YFV17D/HBc or with pDNA-YFV17D/HBc and PEI.

Figure 9:
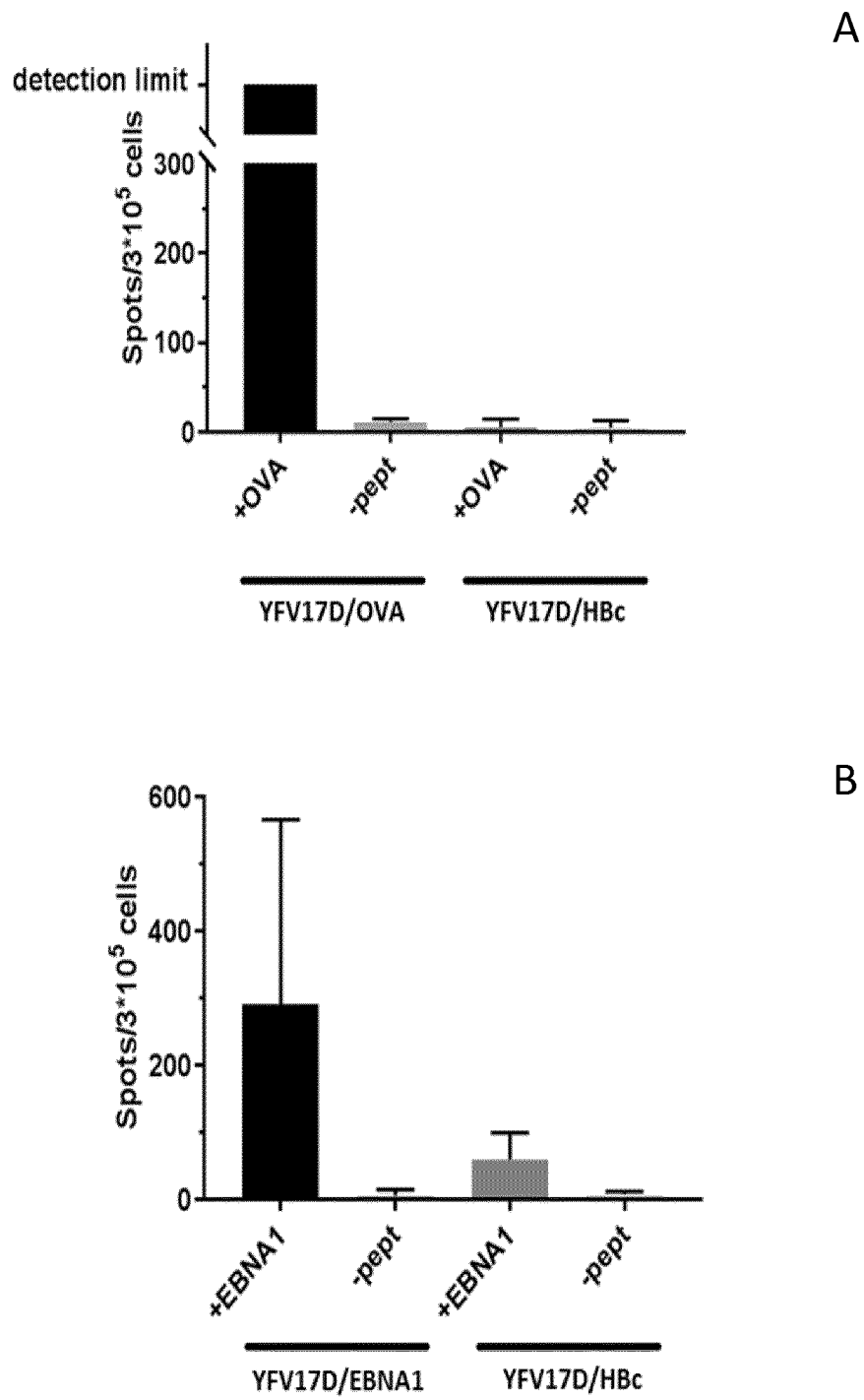

FIG. 9: mouse IFN-γ ELISPOT. A) SFU for splenocytes ($3\times10^5$) isolated from AG129 mice immunized with YFV17D/OVA (and YFV17D/HBc as negative control), stimulated with a peptide derived from chicken ovalbumin (+OVA) or not stimulated (-pept). B) SFU for splenocytes ($3\times10^5$) isolated from AG129 mice immunized with YFV17D/EBNA1 (and YFV17D/HBc as negative control), stimulated with a peptide mixture derived from EBNA1 (+EBNA1) or not stimulated (-pept).

The present invention overcomes the prior art problems using one or more of the following modifications.

A more efficient cleaving peptide has been used namely *Thosea asigna* virus 2A peptide (T2A) [Donnelly et al. (2001) *J Gen Virol* 82, 1027-1041], the use of this peptide also overcomes the need to include a further ubiquitin cleavage sequence. Apart from *Thosea asigna*, other viral 2A peptides can be used in the compounds and methods of the present invention. Examples hereof are described in e.g. Chng et al. (2015) MAbs 7, 403-412, namely APVKQTLNFDLLKLAGDVESNPGP of foot- and mouth disease virus [SEQ ID NO: 38], ATNFSLLKQAGDVEENPGP [SEQ ID NO: 39] of porcine teschovirus-1, and QCTNYALLKLAGDVESNPGP from equine rhinitis A virus [SEQ ID NO: 40]. These peptides have a conserved LxxxGDVExNPGP motif [SEQ ID NO: 17]. Peptides with this consensus sequence can be used in the compounds of the present invention. Other suitable examples of viral 2A cleavage peptides represented by the consensus sequence DXEXNPGP [SEQ ID NO:46] are disclosed in Souza-Moreira et al. (2018) *FEMS Yeast Res.* August 1. Further suitable examples of 2A cleavage peptides from as well picornaviruses as from insect viruses, type C rotaviruses, trypanosome and bacteria (*T. maritima*) are disclosed in Donnelly (2001) *J Gen Virol.* 82, 1027-1041.

The present invention is illustrated with a yellow fever but can be equally performed using other flavivirus based constructs such as but not limited to, Japanese Encephalitis, Dengue, Murray Valley Encephalitis (MVE), St. Louis Encephalitis (SLE), West Nile (WN), Tick-borne Encephalitis (TBE), Russian Spring-Summer Encephalitis (RSSE), Kunjin virus, Powassan virus, Kyasanur Forest Disease virus, Zika virus, Usutu virus, Wesselsbron and Omsk Hemorrhagic Fever virus.

The viral fusion constructs further contains a repeat of the N-terminal part of the Capsid protein. In the present invention the repeat has the same amino acid sequence but the DNA sequence has been modified to include synonymous codons, resulting in a maximally ~75% nucleotide sequence identity over the 21 codons used [herein codon 1 is the start ATG]. As demonstrated by Samsa et al. (2012) J. Virol. 2012 86, 1046-1058 the Capsid N-terminal part may be not limited to the 21 AA Capsid N terminal part, and may comprise for example an additional 5, 10, 15, 20 or 25 amino acids. Prior art only mutated cis-acting RNA structural elements from the repeat [Stoyanov (2010) *Vaccine* 28, 4644-4652]. The approach of the present invention thus also abolishes any possibility for homologous recombination, which leads to an extraordinary stable viral fusion construct.

In typical embodiment the nucleotide sequence encoding the N-terminal part of the capsid protein, which is located 5' of the sequence encoding the epitope or antigen is identical to the sequence of the virus used for the generation of the construct. The mutations which are introduced to avoid recombination are introduced in the nucleotide sequence encoding the N-terminal part of the capsid protein, which is located 3' of the sequence encoding the epitope or antigen.

Furthermore in the repeat of the C gene encoding the Capsid, the sequence only starts from the second codon, which likely affects cleavage from T2A; T2A cleavage is favored in the constructs of the present invention because the amino acid (aa) c terminal of the T2A 'cleavage' site (NPG/P) [SEQ ID NO: 47] is a small aa, namely serine (NPG/PS) [SEQ ID NO: 48] or alternatively Gly, Ala, or Thr instead of the start methionine in the original Capsid protein.

Further also codon-optimized cDNAs are used for the antigens that are cloned flavivirus constructs.

Overall, one or more of the above modifications minimize the replicative burden of inserting extra 'cargo' in the vector that would otherwise unavoidably pose on a fitness cost on YFV replication.

The present invention is illustrated with immunogenic proteins comprising T cell epitopes but is applicable to any immunogenic protein which induce an humoral and/or cell-mediated immune response and include proteins comprising e.g. B cell epitopes or NKT epitopes. Immunogenic proteins can be for example human proteins causing autoimmune diseases or tumor antigens, and animal, plant, bacterial, fungal, or viral antigens causing allergies or infections.

The present invention relates to the use for vaccination purposes of (i) the plasmid DNA molecule encoding a full-length recombinant YFV17D genome containing the coding sequence of the HBcAg, (ii) the infectious RNA molecule that is encoded on said plasmid DNA and (iii) the recombinant live-attenuated virus obtained from cell cultures transfected with said plasmid DNA. The invention also comprises (i) the preparation of the plasmid DNA in bacteria or yeast and (ii) the preparation of the recombinant live-attenuated virus from in vitro cell cultures or rodent tissues. Described herein is the plasmid DNA molecule encoding a full-length recombinant live-attenuated yellow fever virus genome and derivatives thereof for vaccination purposes. Recombinant live-attenuated virus obtained by transfection of said plasmid DNA in in vitro cell cultures expresses hepatitis B virus core antigen and generates both a humoral and cellular immune response in mice lacking both interferon type I and type II receptors.

The propagation of the chimeric constructs prior to attenuation, as well as the cDNA of a construct after attenuation requires an error proof replication of the construct. The use of Bacterial Artificial Chromosomes, and especially the use of inducible BACS as disclosed by the present inventors in WO2014174078, is particularly suitable for high yield, high quality amplification of cDNA of RNA viruses such as chimeric constructs of the present invention.

A BAC as described in this publication BAC comprises:
an inducible bacterial ori sequence for amplification of said BAC to more than 10 copies per bacterial cell, and
a viral expression cassette comprising a cDNA of an the RNA virus genome and comprising cis-regulatory elements for transcription of said viral cDNA in mammalian cells and for processing of the transcribed RNA into infectious RNA virus.

As is the case in the present invention the RNA virus genome is a chimeric viral cDNA construct of two virus genomes.

In these BACS, the viral expression cassette comprises a cDNA of a positive-strand RNA virus genome, an typically
a RNA polymerase driven promoter preceding the 5' end of said cDNA for initiating the transcription of said cDNA, and
an element for RNA self-cleaving following the 3' end of said cDNA for cleaving the RNA transcript of said viral cDNA at a set position.

The BAC may further comprise a yeast autonomously replicating sequence for shuttling to and maintaining said bacterial artificial chromosome in yeast. An example of a yeast ori sequence is the 2μ plasmid origin or the ARS1 (autonomously replicating sequence 1) or functionally homologous derivatives thereof.

The RNA polymerase driven promoter of this first aspect of the invention can be an RNA polymerase II promoter, such as Cytomegalovirus Immediate Early (CMV-IE) promoter, or the Simian virus 40 promoter or functionally homologous derivatives thereof.

The RNA polymerase driven promoter can equally be an RNA polymerase I or III promoter.

The BAC may also comprise an element for RNA self-cleaving such as the cDNA of the genomic ribozyme of hepatitis delta virus or functionally homologous RNA elements.

The formulation of DNA into a vaccine preparation is known in the art and is described in detail in for example chapter 6 to 10 of "DNA Vaccines" Methods in Molecular Medicine Vol 127, (2006) Springer Saltzman, Shen and Brandsma (Eds.) Humana Press. Totoma, N.J. and in chapter 61 Alternative vaccine delivery methods, Pages 1200-1231, of Vaccines (6th Edition) (2013) (Plotkin et al. Eds.). Details on acceptable carrier, diluents, excipient and adjuvant suitable in the preparation of DNA vaccines can also be found in WO2005042014, as indicated below.

"Acceptable carrier, diluent or excipient" refers to an additional substance that is acceptable for use in human and/or veterinary medicine, with particular regard to immunotherapy.

By way of example, an acceptable carrier, diluent or excipient may be a solid or liquid filler, diluent or encapsulating substance that may be safely used in systemic or topic administration. Depending upon the particular route of administration, a variety of carriers, well known in the art may be used. These carriers may be selected from a group including sugars, starches, cellulose and its derivatives, malt, gelatine, talc, calcium sulphate and carbonates, vegetable oils, synthetic oils, polyols, alginic acid, phosphate buffered solutions, emulsifiers, isotonic saline and salts such as mineral acid salts including hydrochlorides, bromides and sulphates, organic acids such as acetates, propionates and malonates and pyrogen-free water.

A useful reference describing pharmaceutically acceptable carriers, diluents and excipients is Remington's Pharmaceutical Sciences (Mack Publishing Co. N. J. USA, (1991)) which is incorporated herein by reference.

Any safe route of administration may be employed for providing a patient with the DNA vaccine. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intramuscular and subcutaneous injection may be appropriate, for example, for administration of immunotherapeutic compositions, proteinaceous vaccines and nucleic acid vaccines. It is also contemplated that microparticle bombardment or electroporation may be particularly useful for delivery of nucleic acid vaccines. Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

DNA vaccines suitable for oral or parenteral administration may be presented as discrete units such as capsules, sachets or tablets each containing a pre-determined amount of plasmid DNA, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the DNA plasmids with liquid carriers or finely divided solid carriers or both, and then, if necessary, shaping the product into the desired presentation.

The above compositions may be administered in a manner compatible with the dosage formulation, and in such amount as is effective. The dose administered to a patient, should be sufficient to effect a beneficial response in a patient over an appropriate period of time. The quantity of agent (s) to be administered may depend on the subject to be treated inclusive of the age, sex, weight and general health condition thereof, factors that will depend on the judgement of the practitioner. Furthermore DNA vaccine may be delivered by bacterial transduction as using live-attenuated strain of *Salmonella* transformed with said DNA plasmids as exemplified by Darji et al. (2000) FEMS Immunol. Med. Microbiol. 27, 341-349 and Cicin-Sain et al. (2003) J. Virol. 77, 8249-8255 given as reference.

Typically the DNA vaccines are used for prophylactic or therapeutic immunisation of humans, but can for certain viruses also be applied on vertebrate animals (typically mammals, birds and fish) including domestic animals such as livestock and companion animals. The vaccination is envisaged of animals which are a live reservoir of viruses (zoonosis) such as monkeys, mice, rats, birds and bats.

In certain embodiments vaccines may include an adjuvant, i.e. one or more substances that enhances the immunogenicity and/or efficacy of a vaccine composition However, life vaccines may eventually be harmed by adjuvants that may stimulate innate immune response independent of viral replication. Non-limiting examples of suitable adjuvants include squalane and squalene (or other oils of animal origin); block copolymers; detergents such as Tween-80; Quill A, mineral oils such as Drakeol or Marcol, vegetable oils such as peanut oil; *Corynebacterium*-derived adjuvants such as *Corynebacterium parvum; Propionibacterium*-derived adjuvants such as *Propionibacterium* acne; *Mycobacterium bovis* (Bacille Calmette and Guerin or BCG); interleukins such as interleukin 2 and interleukin 12; monokines such as interleukin 1; tumour necrosis factor; interferons such as gamma interferon; combinations such as saponin-aluminium hydroxide or Quil-A aluminium hydroxide; liposomes; ISCOMt) and ISCOMATRIX (B) adjuvant; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol'EMA; acrylic copolymer emulsions such as Neocryl A640; vaccinia or animal poxvirus proteins; sub-viral particle adjuvants such as cholera toxin, or mixtures thereof.

Example 1. Materials and Methods

Indirect immunofluorescence assay: For detection of HBcAg expressed from YFV-HBc, baby hamster kidney cells strain 21J (BHK21J) were transfected with PLLAV-YFV-HBc. Per chamber of an 8-chamber slide (Milliwell® EZ slide, Millipore) 50,000 BHK21J cells were seeded and transfected the following day with a mixture of 100 ng PLLAV-YFV-HBc in 9 µl serum-free medium and 0.3 µl TransIT®-LT1 transfection reagent (Mirus® Bio LLC, US). Cells were fixed two days later with 3.7% formaldehyde in PBS, permeabilized with 0.1% Triton X-100 in PBS and subsequently incubated with a polyclonal mouse antibody raised against YFV antigens and a polyclonal rabbit antibody raised against HBcAg at a dilution of 1:500. The YFV antigens and HBcAg were detected with an Alexa Fluor®488-conjugated goat anti-mouse IgG and an Alexa Fluor®647-conjugated donkey anti-rabbit IgG, respectively. Plaque assay: For the visualization of virus plaques, $5\times10^5$ BHK21J cells were used to seed each well of a 12-well polystyrene microplate (Falcon, Corning). The following day these monolayers were incubated with 1 ml of a serial dilution of the virus for 1 hour and subsequently overlayed with a 1:1 mixture of 1% LMP agarose in $dH_2O$ and MEM 2× medium. After 5 days of incubation time at 37° C. and 5% $CO_2$, cells were fixed with 8% formaldehyde in PBS. After removal of the agarose overlay plaques were visualized by staining of the cells with 1% methylene blue in PBS and 10% ethanol.

ELISPOT: To assess whether the YFV-HBc could stimulate splenocytes of immunized mice to secrete IFN-γ, an enzyme-linked immunospot (ELISPOT) assay was performed (mouse IFN gamma ELISPOT Ready-SET-Go!®, eBioscience), according to the manufacturer's protocol. Briefly, polyvinylidene difluoride-backed ninety-six-well plates (Millipore) were coated with an IFN-γ-binding capture antibody and stored overnight at 4° C. Splenocytes were added at a density of $4\times10^5$ cells per well in triplicate. Peptide (5 µg/ml) was used to stimulate the cells. The plates were incubated for 24 hours at 37° C. and 5% $CO_2$. Plates were washed and a biotinylated detection antibody was added. After 2 hours, avidin-HRP was added to the wells and incubated again for 45 minutes before the addition of the substrate AEC, 3-amino-9-ethylcarbazole. The colorimetric reaction was stopped after 10 minutes by washing the plate with $dH_2O$. Spots were counted with an AID ELISPOT reader (Autoimmun Diagnostika GmbH, Germany).

Example 2. Construction and In Vitro Characterization of Recombinant Yellow Fever 17D Virus The construction of a HBc-expressing YFV17D (YFV17D/HBc) was based on a patented reverse genetics system that comprises a full-length YFV17D cDNA as an expression cassette on a bacterial artificial chromosome (BAC) [Dallmeier & Neyts, WO2014/174078A1], henceforth called pShuttle/YFV17D.WO2014174078A1 The viral cDNA was modified to encode the hepatitis B virus core antigen (HBcAg), serotype ayw, nucleotides 1-465. This sequence was inserted in frame into the YFV17D cDNA, preceded upstream by 63 nucleotides encoding the first 21 amino acids of the YFV17D capsid protein, and was followed immediately downstream by a 2A peptide of *Thosea asigna* virus to ensure post-translational cleavage from the YFV17D polypeptide, and by the rest of the viral polyprotein (including the full-length capsid gene, nucleotides 2-10862)[[Stoyanov (2010) *Vaccine* 28, 4644-4652]. To prevent recombination between the two sequences coding for YFV17D capsid upstream and downstream of HBc, synonymous codons were used (FIG. 1). This BAC expressing the YFV17D/HBc will henceforth be referred to as pShuttle/YFV17D/HBc. For the construction of pShuttle/YFV17D/HBc, following cloning steps were performed (schematic map in FIG. 2). First, we inserted an URA3 gene expression cassette upstream of the YFV17D capsid gene, flanked by a TEF promoter and a TEF terminator, upstream and downstream of the URA3 gene, respectively. The rationale behind this is to create a vector which offers increased ease of cloning, by introducing the selection marker URA3 (enabling counter-selection with 5-fluoroorotic acid (5-FOA)). This cassette was preceded upstream by 63 nucleotides encoding the first 21 amino acids of the YFV17D capsid protein and was followed immediately downstream by a 2A peptide of *Thosea asigna* virus (T2A peptide) and the rest of the viral polyprotein. A custom synthesized DNA fragment (gBlock, Integrated DNA Technologies, Leuven, Belgium) encoding this expression cassette was amplified by PCR with primers #3 and #4 (see Table 1 for all primer sequences), and the resulting PCR product was further elongated in subsequent PCRs with primer pairs #5 & #6, #7 & #15 and #15 & #17. The destination plasmid, encoding red fluorescent protein mCherry from the same site in the YFV17D capsid gene (pShuttle/YFV17D/mCherry), was digested with restriction enzyme NotI at a unique site in the plasmid. Both PCR product and restricted destination plasmid (with overlapping ends) were transformed into yeast cells (*S. cerevisiae*, strain YPH500), and recombined in these cells by homologous recombination of the overlapping ends, into pShuttle/YFV17D/URA3. Second, we used the two PmeI sites flanking the URA3 gene to excise URA3 back out of pShuttle/YFV17D/URA3, and transformed this open vector back into yeast, together with a PCR-amplified gBlock encoding the first 155 amino acids of HBc (amplified and elongated in subsequent PCRs with primer pairs #8 & #16, #5 & #6, #15

& #7 and #15 & #17) [or encoding the first 155 amino acids of HBc, followed by the coding sequence of green fluorescent protein LOV [Buckley (2015) Curr. opinion chem. biol. 27, 39-45] (amplified and elongated in subsequent PCRs with primer pairs #8 & #9, #5 & #6, #15 & #7 and #15 & #17)]. By homologous recombination of the overlapping ends of PCR product and digested vector in yeast, this resulted in pShuttle/YFV17D/HBc.

Viability and transgene expression of YFV17D/HBc was assessed by transfection of pDNA-YFV17D/HBc into BHK21J cells. Immunofluorescence staining revealed stable expression of HBc in addition to YFV17D antigens. To determine if the resulting virus YFV17D/HBc stably expressed the transgene, it was passaged consecutively once every 3 days. Immunofluorescence staining showed stable expression of intact HBc up to passage 4 (FIG. 3).

The supernatant after transfection of pDNA-YFV17D/HBc was used in a plaque assay to investigate whether infectious virus was produced, and compared side by side with the parental YFV17D. Five days post-infection, the plaques produced by the recombinant YFV17D/HBc were visibly smaller than those produced by YFV17D (FIGS. 4A and 4B). Kinetics of viral replication was investigated by generation of a growth curve of YFV17D/HBc and YFV17D by infection of BHK21J cells (MOI 0.01) and titration of supernatant collected over the course of five days (FIG. 4C).

Example 3. Cellular Immune Response in Mice Immunized with YFV17D/HBc

To determine if YFV17D/HBc could prime an immune response in vivo, three AG129 mice (lacking both type I and type II interferon (IFN) receptors) were immunized i.p. with $4.5 \times 10^4$ plaque forming units (PFU) and boosted with $4.5 \times 10^4$ PFU after two weeks. As AG129 generally do not survive an injection with YFV17D, a single injection ($9 \times 10^4$ PFU) of a chimeric YFV/Japanese encephalitis virus vaccine strain (Chimerivax-JE) was used as negative control (2 mice). To detect levels of HBc-specific IFN-γ secretion by peptide-stimulated T-cells, the mice were sacrificed seven weeks after the first injection and their splenocytes used in a mouse IFN-γ enzyme-linked immunospot assay (ELISPOT). Splenocytes were stimulated with peptides derived from either HBcAg or HBsAg. Spot counts were distinctly higher when splenocytes from YFV17D/HBc-immunized mice were stimulated with HBcAg-derived peptides compared to stimulation with HBsAg-derived peptides, or stimulation of splenocytes from the negative control group with either peptide (FIGS. 5A and 5B).

Example 4. Humoral Immune Response in Mice Immunized with YFV17D/HBc

To investigate whether immunization with YFV17D/HBc could mount an antibody response against the HBc transgene, three AG129 mice were immunized i.p. with $7.5 \times 10^4$ PFU YFV17D/HBc and boosted five weeks later ($4.5 \times 10^4$ PFU). Before the first injection and three weeks after the booster, serum was collected and used in an immunofluorescence assay on HBV-infected human hepatoma cells. The use of serum collected after immunization resulted in a marked increase in fluorescence intensity compared to the use of preserum (FIG. 6).

Example 5. Homologous Prime-Boost of YFV17D/HBc

To determine the significance of delivering a homologous booster dose of YFV17D/HBc to HBc-specific T cell levels, mice were vaccinated once or twice (two weeks after the first dose) with $10^4$ pfu of YFV17D/HBc. Splenocytes were harvested four weeks after the first dose of YFV17D/HBc and stimulated with HBc-derived peptides in a mouse IFNγ ELISPOT assay. Spot counts for YFV17D/HBc double-vaccinated mice were not significantly higher than those of single-vaccinated mice. Two shots of 10 µg recombinant HBc (rHBc, American Research Products Inc, Waltham, Mass., USA) adjuvanted by 10 µg of Quil-A® (InvivoGen, San Diego, Calif., USA) did not elicit higher levels of IFNγ-secreting T cells than our vaccine candidate (FIG. 7).

Example 6. Mounting of HBc-Specific T Cell Responses by Vaccination with pDNA-YFV17D/HBc As mentioned above, transfection of YFV17D/HBc-encoding plasmid DNA (pDNA-YFV17D/HBc) in BHK21J results in release of infectious virus (YFV17D/HBc) in the cell culture supernatant, which can be used directly to inoculate mice. We have administered pDNA-YFV17D/HBc to AG129 mice as such, by two intraperitoneal injections of a mixture of this plasmid (3 µg) and in vivo transfection reagent polyethylene imine (PEI), separated by one week. Two weeks after the first injection, mice were sacrificed and their splenocytes used in a mouse IFNγ ELISPOT assay, which showed that HBc-specific T cells had been elicited by pDNA-YFV17D/HBc (FIG. 8).

Example 7. Mounting of Specific T Cell Responses Against Other Antigens Expressed from the Capsid Gene of YFV17D Other T cell antigens were cloned into the site of the YFV17D capsid gene, as described above, namely the full-length chicken ovalbumin (OVA) and the full-length Epstein-Barr virus nuclear antigen 1 (EBNA1).

The OVA insert was amplified by PCR from a gBlock (Integrated DNA Technologies, Leuven, Belgium) which contained the coding sequence of the full-length chicken ovalbumin, flanked on its 5' end by the coding sequence of the first 21 amino acids of the YFV17D capsid protein, and on its 3' end by the coding sequence of the T2A peptide, with primers #1 and #2 (see Table 1 for all primer sequences), and elongated by subsequent PCRs with primer pairs #5 & #7, and #15 & #17. Then, pShuttle/YFV17D/OVA was made by homologous recombination in yeast of the PCR insert and PmeI-restricted pShuttle/YFV17D/URA3 destination plasmid, as described for pShuttle/YFV17D/HBc.

The EBNA1 insert was amplified by PCR from a plasmid which contained the coding sequence of the full-length EBNA1 (kindly provided by professor Christian Münz, University of Zürich) with primers #9 and #10, and elongated by subsequent PCRs with primer pairs #5 & #6, and #15 & #17. Then, pShuttle/YFV17D/EBNA1 was made by homologous recombination in yeast of the PCR insert and PmeI-restricted pShuttle/YFV17D/URA3 destination plasmid, as described for pShuttle/YFV17D/HBc. Both pShuttle/YFV17D/OVA and pShuttle/YFV17D/EBNA1 were transfected in BHK21J, as described for pShuttle/YFV17D/HBc, resulting in the release of infectious virus in the supernatant, henceforth called YFV17D/OVA and YFV17D/EBNA1, respectively.

To investigate the T cell responses elicited by YFV17D/OVA and YFV17D/EBNA1 in vivo, three AG129 mice were immunized once i.p. with $1 \times 10^6$ TCID$_{50}$ of YFV17D/OVA and three AG129 mice were immunized once i.p. with $1 \times 10^6$ $TCID_{50}$ of YFV17D/EBNA1. A single injection ($1\times10^6$ $TCID_{50}$) of YFV17D/HBc was used as negative control (3 AG129 mice). To detect levels of HBc-specific IFN-γ secretion by peptide-stimulated T-cells, the mice were sacrificed five weeks later and their splenocytes were used in a mouse IFNγ ELISPOT. For the mice vaccinated with YFV17D/OVA, splenocytes were stimulated with 5 μg of mixture of peptides derived from EBNA1 (kindly provided by professor Christian Münz, University of Zürich). Both YFV17D/OVA and YFV17D/EBNA1 elicited strong and specific IFNγ responses to peptides of ovalbumin and EBNA1, respectively (FIG. 9).

TABLE 1

Primer sequences

| Primer | Sequence (5' to 3') | SEQ ID NO: |
|---|---|---|
| #1 | aagctcaggg aaaaaccctg ggcgtcaata tggtacgacg aggagttcgc ggatcc | 19 |
| #2 | gtgtcttacc ctgggctttg cggccgctag gaccggggtt ctcctccacg tcgccacagg | 20 |
| #3 | gtcaatatgg tacgacgagg agttcgcgga tccgtttaaa cctcgtcccc gccgggtcac | 21 |
| #4 | gtcgccacag gtcagcaggg acccgcgtcc ctcgtttaaa cagtatagcg accagcattc | 22 |
| #5 | cagaacatgt ctggtcgtaa agctcaggga aaaaccctgg gcgtcaatat ggtacgacga | 23 |
| #6 | accctgggct ttgcggccgc taggaccggg gttctcctcc acgtcgccac aggtcagcag | 24 |
| #7 | ccggacgccg cgacgaacca tgttcacgcc cagtgtctta ccctgggctt tgcggccgct | 25 |
| #8 | cctgggcgtc aatatggtac gacgaggagt tcgcggatcc atggacatcg acccttataa | 26 |
| #9 | cctccacgtc gccacaggtc agcagggacc cgcgtccctc cgcgagggcc tttccctcgg | 27 |
| #10 | gtcttaccct gggctttgcg gccgctagga ccggggttct cctccacgtc gccacaggtc | 28 |
| #11 | tggaggagaa ccccggtcct agcggccgca aagcccaggg taagacactg ggcgtgaaca | 29 |
| #12 | taagacactg ggcgtgaaca tggttcgtcg cggcgtccgg tccttgtcaa acaaaataaa | 30 |
| #13 | tgacgcccag ggtttttccc tgagctttac gaccagacat gttctggtca gttctctgct | 31 |
| #14 | tcgatgtcca tggatccgcg aactcctcgt cgtaccatat tgacgcccag ggtttttccc | 32 |
| #15 | tggattaatt ttaatcgttc gttgagcgat tagcagagaa ctgaccagaa catgtct | 33 |
| #16 | cctccacgtc gccacaggtc agcagggacc cgcgtccctc ggacctgcct cgtcgtc | 34 |
| #17 | tgtttccaat ttgttttgtt ttttgtttta ttttgtttga caaggaccgg acgccgcgac | 35 |
| #18 | gggcgtcaat atggtacgac gaggagttcg cggatccatg ggtagaaggc catttttcca | 36 |
| #19 | cctccacgtc gccacaggtc agcagggacc cgcgtccctc ctcctgccct tcctcaccct | 37 |

Sequence of Interest of pShuttle/YFV17D/URA3

Legend:

| | |
|---|---|
| UPPER CASE | YFV17D 5'-UTR |
| UNDERLINED UPPER CASE | coding sequence of first 21 amino acids of YFV17D capsid protein |
| *Lower case italics* | BamHI site |
| *UPPER CASE ITALICS* | TEF promotor and TEF terminator |
| BOLD UPPER CASE | URA3 gene |
| Underlined lower case | coding sequence of T2A (Thosea asigna 2A) peptide |
| Lower case | coding sequence of YFV17D genome, starting from amino acid #2 |

SEQ ID NO: 1

AGTAAATCCTGTGTGCTAATTGAGGTGCATTGGTCTGCAAATCGAGTTGC

TAGGCAATAAACACATTTGGATTAATTTTAATCGTTCGTTGAGCGATTAG

CAGAGAACTGACCAGAACATGTCTGGTCGTAAAGCTCAGG

M S G R K A Q

SEQ ID NO: 2

GAAAAACCCTGGGCGTCAATATGGTACGACGAGGAGTTCGC*ggatccGTT*

G K T L G V N M V R R G V R

*TAAACCTCGTCCCCGCCGGGTCACCCGGCCAGCGACATGGAGGCCCAGAA*

*TACCCTCCTTGACAGTCTTGACGTGCGCAGCTCAGGGGCATGATGTGACT*

*GTCGCCCGTACATTTAGCCCATACATCCCCATGTATAATCATTTGCATCC*

*ATACATTTTGATGGCCGCACGGCGCGAAGCAAAAATTACGGCTCCTCGCT*

*GCAGACCTGCGAGCAGGGAAACGCTCCCCTCACAGACGCGTTGAATTGTC*

*CCCACGCCGCGCCCCTGTAGAGAAATATAAAAGGTTAGGATTTGCCACTG*

*AGGTTCTTCTTTCATATACTTCCTTTTAAAATCTTGCTAGGATACAGTTC*

*TCACATCACATCCGAACATAAACAACC*ATGACAGTCAACACTAAGACCTA

M T V N T K T Y

TAGTGAGAGAGCAGAAACTCATGCCTCACCAGTAGCACAA

S E R A E T H A S P V A Q

SEQ ID NO: 3

CGATTATTTCGATTAATGGAACTGAAGAAAACCAATTTATGTGCATCAAT

R L F R L M E L K K T N L C A S I

TGATGTTGATACCACTAAGGAATTCCTTGAATTAATTGATAAATTGGGTC

D V D T T K E F L E L I D K L G P

CTTATGTATGCTTAATCAAGACTCATATTGATATAATCAATGATTTTTCC

Y V C L I K T H I D I I N D F S

TATGAATCCACTATTGAACCATTATTAGAACTTTCACGTAAACATCAATT

Y E S T I E P L L E L S R K H Q F

TATGATTTTTGAAGATAGAAAATTTGCTGATATTGGTAATACCGTGAAGA

M I F E D R K F A D I G N T V K K

AACAATATATTGGTGGAGTTTATAAAATTAGTAGTTGGGCAGATATTACT

Q Y I G G V Y K I S S W A D I T

-continued

```
AATGCTCATGGTGTCACTGGGAATGGAGTAGTTGAAGGATTAAAACAGGG
 N  A  H  G  V  T  G  N  G  V  V  E  G  L  K  Q  G
AGCTAAAGAAACCACCACCAACCAAGAGCCAAGAGGGTTATTGATGTTAG
 A  K  E  T  T  T  N  Q  E  P  R  G  L  L  M  L  A
CTGAATTATCATCAGTGGGATCATTAGCATATGGAGAATATTCTCAAAAA
 E  L  S  S  V  G  S  L  A  Y  G  E  Y  S  Q  K
ACTGTTGAAATTGCTAAATCCGATAAGGAATTTGTTATTGGATTTATTGC
 T  V  E  I  A  K  S  D  K  E  F  V  I  G  F  I  A
CCAACGTGATATGGGTGGACAAGAAGAAGGATTTGATTGGCTTATTATGA
 Q  R  D  M  G  G  Q  E  E  G  F  D  W  L  I  M  T
CACCTGGAGTTGGATTAGATGATAAAGGTGATGGATTAGGACAACAATAT
 P  G  V  G  L  D  D  K  G  D  G  L  G  Q  Q  Y
AGAACTGTTGATGAAGTTGTTAGCACTGGAACTGATATTATCATTGTTGG
 R  T  V  D  E  V  V  S  T  G  T  D  I  I  I  V  G
TAGAGGATTGTTTGGTAAAGGAAGAGATCCAGATATTGAAGGTAAAAGGT
 R  G  L  F  G  K  G  R  D  P  D  I  E  G  K  R  Y
ATAGAGATGCTGGTTGGAATGCTTATTTGAAAAAGACTGGCCAATTATAA
 R  D  A  G  W  N  A  Y  L  K  K  T  G  Q  L  *
TCAGTACTGACAATAAAAAGATTCTTGTTTTCAAGAACTTGTCATTTGTA
TAGTTTTTTTATATTGTAGTTGTTCTATTTTAATCAAATGTTAGCGTGAT
TTATATTTTTTTCGCCTCGACATCATCTGCCCAGATGCGAAGTTAAGTG
CGCAGAAAGTAAATATCATGCGTCAATCGTATGTGAATGCTGGTCGCTATA
CTGTTTAAACgagggacgcgggtccctgct
              E  G  R  G  S  L  L
                                          SEQ ID NO: 4
Gacctgtggcgacgtggaggagaaccccggtcctagcggccgcaaagccc
 T  C  G  D  V  E  E  N  P  G  P  S  G  R  K  A  Q
agggtaagacactgggcgtgaacatggttcgtcgcggcgtccggtccttg
 G  K  T  L  G  V  N  M  V  R  R  G  V  R  S  L
tcaaacaaaataaaacaaaaaacaaaacaaattg
 S  N  K  I  K  Q  K  T  K  Q  I
```

Sequence of Interest of pShuttle/YFV17D/HBc
Legend:

| | |
|---|---|
| UPPER CASE | YFV17D 5'-UTR |
| UNDERLINED UPPER CASE | coding sequence of first 21 amino acids of YFV17D capsid protein |
| Lower case italics | BamHI site |
| BOLD UPPER CASE | HBc coding sequence |
| Underlined lower case | coding sequence of T2A (Thosea asigna 2A) peptide |
| Lower case | coding sequence of YFV17D genome, starting from amino acid #2 |

```
                                          SEQ ID NO: 5
AGTAAATCCTGTGTGCTAATTGAGGTGCATTGGTCTGCAAATCGAGTTGC
TAGGCAATAAACACATTTGGATTAATTTTAATCGTTCGTTGAGCGATTAG
CAGAGAACTGACCAGAACATGTCTGGTCGTAAAGCTCAGG
                      M  S  G  R  K  A  Q  G
                                          SEQ ID NO: 6
GAAAAACCCTGGGCGTCAATATGGTACGACGAGGAGTTCGCggatccATG
                                                 K
 T  L  G  V  N  M  V  R  R  G  V  R  G  S  M
GACATCGACCCTTATAAAGAATTTGGAGCTACTGTGGAGTTACTCTCGTT
 D  I  D  P  Y  K  E  F  G  A  T  V  E  L  L  S  F
TTTGCCTTCTGACTTCTTTCCTTCAGTACGAGATCTTCTAGATACCGCCT
 L  P  S  D  F  F  P  S  V  R  D  L  L  D  T  A  S
CAGCTCTGTATCGGGAAGCCTTAGAGTCTCCTGAGCATTGTTCACCTCAC
 A  L  Y  R  E  A  L  E  S  P  E  H  C  S  P  H
CATACTGCACTCAGGCAAGCAATTCTTTGCTGGGGGAACTAATGACTCT
 H  T  A  L  R  Q  A  I  L  C  W  G  E  L  M  T  L
AGCTACCTGGGTGGGTGTTAATTTGGAAGATCCAGCGTCTAGAGACCTAG
 A  T  W  V  G  V  N  L  E  D  P  A  S  R  D  L  V
TAGTCAGTTATGTCAACACTAATATGGGCCTAAAGTTCAGGCAACTCTTG
 V  S  Y  V  N  T  N  M  G  L  K  F  R  Q  L  L
TGGTTTCACATTTCTTGTCTCACTTTTGGAAGAGAAACAGTTATAGAGTA
 W  F  H  I  S  C  L  T  F  G  R  E  T  V  I  E  Y
TTTGGTGTCTTCGGAGTGTGGATTCGCACTCCTCCAGCTTATAGACCAC
 L  V  S  F  G  V  W  I  R  T  P  P  A  Y  R  P  P
CAAATGCCCCTATCCTATCAACACTTCCGGAGACTACTGTTGTTAGACGA
 N  A  P  I  L  S  T  L  P  E  T  T  V  V  R  R
CGAGGCAGGTCCgagggacgcgggtccctgctgacctgtggcgacgtgga
 R  G  R  S  E  G  R  G  S  L  L  T  C  G  D  V  E
ggagaaccccggtcctagcggccgcaaagcccagggtaagacactgggcg
 E  N  P  G  P  S  G  R  K  A  Q  G  K  T  L  G  V
tgaacatggttcgtcgcggcgtccggtccttgtcaaacaaaataaacaa
 N  M  V  R  R  G  V  R  S  L  S  N  K  I  K  Q  K
aaaacaaaacaaattg
 T  K  Q  I  *
                                          SEQ ID NO: 7
  1 mdidpykefg asvellsflp sdffpsirdl ldtasalyre
    alespehcsp hhtalrqail
 61 cwgelmnlat wvggnledpa sreavvsyvn vnmglkirql
    lwfhiscltf gretvleylv
121 sfgvwirtpp ayrpqnapil stlpettvvr rrgr
```

Sequence of Interest of pShuttle/YFV17D/O

Sequence of Interest of pShuttle/YFV17D/EBNA1
Legend:

| | |
|---|---|
| UPPER CASE | YFV17D 5'-UTR |
| UNDERLINED UPPER CASE | coding sequence of first 21 amino acids of YFV17D capsid protein |
| Lower case italics | BamHI site |
| BOLD UPPER CASE | EBNA1 coding sequence |
| Underlined lower case | coding sequence of T2A (Thosea asigna 2A) peptide |
| Lower case | coding sequence of YFV17D genome, starting from amino acid #2 |

SEQ ID NO: 11
AGTAAATCCTGTGTGCTAATTGAGGTGCATTGGTCTGCAAATCGAGTTGC

TAGGCAATAAACACATTTGGATTAATTTTAATCGTTCGTTGAGCGATTAG

CAGAGAACTGACCAGAAC<u>ATGTCTGGTCGTAAAGCTCAGG</u>

M  S  G  R  K  A  Q  G

SEQ ID No: 12
<u>GAAAAACCCTGGGCGTCAATATGGTACGACGAGGAGTTCGC</u>*ggatcc*GGT

K  T  L  G  V  N  M  V  R  R  G  V  R  G  S  G

AGAAGGCCATTTTTCCACCCTGTAGGGGAAGCCGATTATTTTGAATACCA

R  R  P  F  F  H  P  V  G  E  A  D  Y  F  E  Y  H

CCAAGAAGGTGGCCCAGATGGTGAGCCTGACGTGCCCCCGGGAGCGATAG

Q  E  G  G  P  D  G  E  P  D  V  P  P  G  A  I  E

AGCAGGGCCCCGCAGATGACCCAGGAGAAGGCCCAAGCACTGGACCCCGG

Q  G  P  A  D  D  P  G  E  G  P  S  T  G  P  R

GGTCAGGGTGATGGAGGCAGGCGCAAAAAAGGAGGGTGGTTTGGAAAGCA

G  Q  G  D  G  G  R  R  K  K  G  G  W  F  G  K  H

TCGTGGTCAAGGAGGTTCCAACCCGAAATTTGAGAACATTGCAGAAGGTT

R  G  Q  G  G  S  N  P  K  F  E  N  I  A  E  G  L

TAAGAGCTCTCCTGGCTAGGAGTCACGTAGAAAGGACTACCGACGAAGGA

R  A  L  L  A  R  S  H  V  E  R  T  T  D  E  G

ACTTGGGTCGCCGGTGTGTTCGTATATGGAGGTAGTAAGACCTCCCTTTA

T  W  V  A  G  V  F  V  Y  G  G  S  K  T  S  L  Y

CAACCTAAGGCGAGGAACTGCCCTTGCTATTCCACAATGTCGTCTTACAC

N  L  R  R  G  T  A  L  A  I  P  Q  C  R  L  T  P

CATTGAGTCGTCTCCCCTTTGGAATGGCCCCTGGACCCGGCCCACAACCT

L  S  R  L  P  F  G  M  A  P  G  P  G  P  Q  P

GGCCCGCTAAGGGAGTCCATTGTCTGTTATTTCATGGTCTTTTTACAAAC

G  P  L  R  E  S  I  V  C  Y  F  M  V  F  L  Q  T

TCATATATTTGCTGAGGTTTTGAAGGATGCGATTAAGGACCTTGTTATGA

H  I  F  A  E  V  L  K  D  A  I  K  D  L  V  M  T

CAAAGCCCGCTCCTACCTGCAATATCAGGGTGACTGTGTGCAGCTTTGAC

K  P  A  P  T  C  N  I  R  V  T  V  C  S  F  D

GATGGAGTAGATTTGCCTCCCTGGTTTCCACCTATGGTGGAAGGGGCTGC

D  G  V  D  L  P  P  W  F  P  P  M  V  E  G  A  A

CGCGGAGGGTGATGACGGAGATGACGGAGATGAAGGAGGTGATGGAGATG

A  E  G  D  D  G  D  D  G  D  E  G  G  D  G  D  E

AGGGTGAGGAAGGGCAGGAG<u>gagggacgcgggtcctgctgacctgtggc</u>

G  E  E  G  Q  E  E  G  R  G  S  L  L  T  C  G

<u>gacgtggaggagaaccccggtcct</u>agcggccgcaaagcccagggtaagac

D  V  E  E  N  P  G  P  S  G  R  K  A  Q  G  K  T actgggcgtgaacatggttcgtcgcggcgtccggtccttgtcaaacaaaa

L  G  V  N  M  V  R  R  G  V  R  S  L  S  N  K  I taaaacaaaaaacaaaacaaattg

K  Q  K  T  K  Q  I

SEQ ID NO: 13
```
  1 pffhpvgead yfeylqeggp dgepdvppga ieqgpaddpg
    egpstgprgq gdggrrkkgg 61 wfgkhrgqgg snpkfeniae glrvllarsh vertteegtw
    vagvfvyggs ktslynlrrg 121 talaipqcrl tplsrlpfgm apgpgpqpgp lresivcyfm
    vflqthifae vlkdaikdlv 181 mtkpaptcni kvtvcsfddg vdlppwfppm vegaaaegdd
    gddgdeggdg degeegqe
```

Capsid Synonymous Codons Sequences:

(SEQ ID NO: 14)
atgtctggtcgtaaagctcagggaaaaaccctgggcgtcaatatggtacg acgaggagttcgc (SEQ ID NO: 15)
agcggccgcaaagcccagggtaagacactgggcgtgaacatggttcgtcg cggcgtccgg.

---

The invention claimed is:

1. A polynucleotide comprising a sequence of a flavivirus wherein a nucleotide sequence encoding the sequence of the flavivirus is preceded by a sequence encoding:
   a part of a flavivirus Capsid protein comprising or consisting of an N terminal part of the flavivirus Capsid protein,
   an immunogenic protein, or a part thereof comprising an immunogenic peptide, and
   a 2A cleaving peptide, wherein the 2A cleaving peptide is not followed by ubiquitin.

2. The polynucleotide according to claim 1, wherein the part of the flavivirus Capsid protein comprises or consists of 21 N terminal amino acids of the flavivirus Capsid protein.

3. The polynucleotide according to claim 1, wherein the nucleotide sequence encoding the N terminal part of the capsid gene has one or more synonymous codons compared with a corresponding sequence in a full length viral sequence.

4. The polynucleotide according to claim 1, wherein the flavivirus is Yellow Fever virus.

5. The polynucleotide according to claim 1, wherein the flavivirus is Yellow Fever virus, and wherein the N terminal part of the Yellow Fever virus Capsid protein consists of the sequence of SEQ ID NO: 2.

6. The polynucleotide according to claim 1, wherein the 2A cleaving peptide is a *Thosea asigna* 2A peptide with an amino acid sequence of SEQ ID NO: 16.

7. The polynucleotide according to claim 1, wherein the immunogenic protein is a T cell antigen and the immunogenic part thereof comprises a T cell epitope.

8. The polynucleotide according to claim 1, wherein codon usage of the immunogenic protein of immunogenic part thereof is adapted for expression in bacteria.

9. The polynucleotide according to claim 1, which is a Bacterial Artificial Chromosome (BAC).

10. The polynucleotide according to claim 1, which is a Bacterial Artificial Chromosome (BAC) comprising an inducible bacterial ori sequence for amplification of the BAC to more than 10 copies per bacterial cell, and a viral expression cassette comprising a cDNA of the polynucleotide and comprising cis-regulatory elements for transcription of viral cDNA in mammalian cells and for processing of transcribed RNA into infectious RNA virus.

11. The polynucleotide according to claim 1, wherein the immunogenic protein is a T cell antigen, and the T cell antigen is selected from the group consisting of a core antigen of HBC, OVA and EBNA1.

12. A flavivirus fusion construct, wherein the flavivirus is preceded at its aminoterminus by:
- a part of a flavivirus Capsid protein comprising or consisting of an N terminal part of the flavivirus Capsid protein,
- an immunogenic protein, or a part thereof comprising an immunogenic peptide, and
- a 2A cleaving peptide, wherein the 2A cleaving peptide is not followed by ubiquitin.

13. A flavivirus fusion construct according to claim 12, wherein the part of the flavivirus Capsid protein comprises or consists of 21 N terminal amino acids of the flavivirus Capsid protein.

14. The flavivirus fusion construct according to claim 12, wherein the flavivirus is Yellow Fever virus.

15. The flavivirus fusion construct according to claim 12, wherein the flavivirus is Yellow Fever virus, and wherein the N terminal part of the Yellow Fever virus capsid consists of the sequence of SEQ ID NO: 2.

16. The flavivirus fusion construct according to claim 12, wherein the 2A cleaving peptide is *Thosea asigna* 2A peptide with an amino acid sequence of SEQ ID NO: 16.

17. The flavivirus fusion construct according to claim 12, wherein the immunogenic protein is a T cell antigen and the immunogenic part thereof comprises a T cell epitope.

18. The flavivirus fusion construct according to claim 12, wherein the flavivirus is Yellow Fever virus, and wherein the Yellow Fever virus is YF17D attenuated virus.

19. The flavivirus fusion construct according to claim 12, wherein the immunogenic protein is selected from the group consisting of a core antigen of HBC, OVA and EBNA1.

20. The flavivirus fusion construct according to claim 19, wherein the core antigen of HBC comprises an amino acid sequence of SEQ ID NO: 7, or a fragment thereof comprising a T cell epitope.

21. A pharmaceutical comprising a flavivirus fusion construct according to claim 12, and a pharmaceutical acceptable carrier.

22. A method of provoking an immune response to an immunogenic protein, the method comprising administering an effective amount of a flavivirus fusion construct according to claim 12 to a subject in need thereof.

* * * * *

UNITED STATES PATENT AND TRADEMARK OFFICE
CERTIFICATE OF CORRECTION

PATENT NO. : 11,680,084 B2
APPLICATION NO. : 16/753364
DATED : June 20, 2023
INVENTOR(S) : Robbert Boudewijns, Kai Dallmeier and Johan Neyts It is certified that error appears in the above-identified patent and that said Letters Patent is hereby corrected as shown below:

On the Title Page

Item (54), delete "LIVE-ATTENUATED FLAVIRUSES WITH HETEROLOGOUS ANTIGENS", and insert --LIVE-ATTENUATED FLAVIVIRUSES WITH HETEROLOGOUS ANTIGENS--, therefor.

Column 2, item (56), other publications, cite no. 6, delete "vims", and insert --virus--, therefor.

Column 2, item (74), attorney, agent, or firm, delete "Dinsmore & Shohl, LLP", and insert --Dinsmore & Shohl LLP--, therefor.

Column 2, item (57), abstract, Line(s) 4, after "comprising", delete "a".

In the Specification

In Column 1, Line(s) 1, delete "LIVE-ATTENUATED FLAVIRUSES WITH HETEROLOGOUS ANTIGENS", and insert --LIVE-ATTENUATED FLAVIVIRUSES WITH HETEROLOGOUS ANTIGENS--, therefor.

In Column 3, Line(s) 39, after "depending", delete "of", and insert --on--, therefor.

In Column 3, Line(s) 43, after "depending", delete "from", and insert --on--, therefor.

In Column 6, Line(s) 52, after "following", delete "an" and insert --a--, therefor.

In Column 8, Line(s) 44, before "humoral", delete "an", and insert --a--, therefor.

In Column 9, Line(s) 12, after "cDNA of", delete "an".

Signed and Sealed this
Twenty-first Day of November, 2023

Katherine Kelly Vidal
*Director of the United States Patent and Trademark Office*

In Column 9, Line(s) 21, before "typically", delete "an" and insert --a--, therefor.

In Column 12, Line(s) 29, before "[Stoyanov", delete "[".